(12) United States Patent
Huang

(10) Patent No.: US 7,186,504 B2
(45) Date of Patent: Mar. 6, 2007

(54) CELLS FOR DETECTION OF ENTEROVIRUSES

(75) Inventor: Yung T. Huang, Richmond Heights, OH (US)

(73) Assignee: University Hospitals of Cleveland, Cleveland, OH (US)

( * ) Notice: Subject to any disclaimer, the term of this patent is extended or adjusted under 35 U.S.C. 154(b) by 393 days.

(21) Appl. No.: 10/861,724

(22) Filed: Jun. 3, 2004

(65) Prior Publication Data

US 2004/0259243 A1 Dec. 23, 2004

Related U.S. Application Data

(62) Division of application No. 09/844,311, filed on Apr. 27, 2001, now Pat. No. 6,821,741.

(51) Int. Cl.
*C12Q 1/70* (2006.01)
*C12N 7/00* (2006.01)
*C12N 7/02* (2006.01)

(52) U.S. Cl. ........................ 435/5; 435/239; 435/235.1

(58) Field of Classification Search .................... 435/5, 435/239, 235.1
See application file for complete search history.

(56) References Cited

U.S. PATENT DOCUMENTS

| | | | | |
|---|---|---|---|---|
| 5,686,305 | A | 11/1997 | Wang et al. | 435/348 |
| 5,811,282 | A | 9/1998 | Chesebro et al. | 435/240.23 |
| 5,939,253 | A | 8/1999 | Scholl et al. | 435/5 |
| 5,985,642 | A | 11/1999 | Foster et al. | 435/239 |
| 5,989,805 | A | 11/1999 | Reilly et al. | 435/5 |
| 6,168,915 | B1 | 1/2001 | Scholl et al. | 435/5 |

OTHER PUBLICATIONS

Bergelson et al., "Decay-Accelerating Factor (CDSS), a Glycosylphosphatidylinositol-Anchored Complement Regulatory Protein, is a Receptor for Several Echoviruses," *Proc Natl Acad Sci USA*, 91:6245-6248 (1994).
Bergelson et al., "Coxsackievirus B3 Adapted to Growth in RD Cells Binds to Decay-Accelerating Factor (CD55)," *J Virol.* 69:1903-1906 (1995).
Clarkson et al., "Characterization of the Echovirus 7 Receptor: Domains of CD55 Critical for Virus Binding," *J Virol*, 69:5497-5501 (1995).
Karnauchow et al., "The HeLa Cell Receptor for Enterovirus 70 Is Decay-Accelerating Factor (CD55)," *J Virol*, 70:5143-5152 (1996).
Karnauchow et al., "Short Consensus Repeat Domain I of Decay-Accelerating Factor Is Required for Enterovirus 70 Binding," *J Virol*, 72:9380-9383 (1998).
Martino et al., "Cardiovirulent Coxsackieviruses and the Decay-Accelerating Factor (CD55) Receptor," Virol, 244:302-314 (1998).
Powell et al., "Characterization of echoviruses that bind decay accelerating factor (CD55): evidence that some haemagglutinating strains use more than one cellular receptor," *J Gen Virol*, 79:1707-1713 (1998).
Powell et al., "Mapping the binding domains on decay accelerating factor (DAF) for haemagglutinating enteroviruses: implications for the evolution of a DAF-binding phenotype," *J Gen Virol*, 80:3145-3152 (1999.
Shafren et al., "Coxsackieviruses B1, B3, and B5 Use Decay Accelerating Factor as a Receptor for Cell Attachment," *J Virol*, 69:3873-3877 (1995).
Shafren et al., "Coxsackievirus A21 Binds to Decay-Accelerating Factor but Requires Intercellular Adhesion Molecule 1 for Cell Entry," *J Virol*, 71::4736-4743 (1997).
GenBank Accession No. M15799.
Hierholzer et al., "Sensitivity of NCI-H292 Human Lung Mucoepidermoid Cells for Respiratory and Other Human Viruses," *J Clin Microbiol.* 31:1504-1510 (1993).
Spiller et al., "Echoviruses and Coxsackie B Viruses That Use Human Decay-Accelerating Factor (DAF) as a Receptor Do Not Bind the Rodent Analogues of DAF," *J Infect Dis*, 181:340-343 (2000).
Ward et al., "Decay-accelerating factor CD55 is identified as the receptor for echovirus 7 using CELICS, a rapid immuno-focal cloning method," *EMBO J*, 13:5070-5074 (1994).

*Primary Examiner*—Mary E. Mosher
*Assistant Examiner*—Bo Peng
(74) *Attorney, Agent, or Firm*—Medlen & Carroll LLP

(57) ABSTRACT

The invention provides cell lines which are useful for the rapid detection of enteroviruses. In particular, the invention provides transgenic African green monkey kidney cell lines and buffalo green monkey kidney cell lines. The invention provides cell lines which have increased sensitivity to infection by enteroviruses in single-cell type and mixed-cell type cultures compared to other cell types which are currently used for enterovirus detection. The cells of the invention also are permissive to infection by a larger number of enteroviruses as compared to the cell type from which they were derived.

55 Claims, 5 Drawing Sheets
(2 of 5 Drawing Sheet(s) Filed in Color)

```
   1 ccgagcgtgc ccgcggcgct gccccctcctc ggggagctgc cccggctgct gctgctggtg
  61 ctgttgtgcc tgccggccgt gtggggtgac tgtggccttc ccccagatgt acctaatgcc
 121 cagccagctt tggaaggccg tacaagtttt cccgaggata ctgtaataac gtacaaatgt
 181 gaagaaagct ttgtgaaaat tcctggcgag aaggactcag tgacctgcct taagggcatg
 241 caatggtcag atattgaaga gttctgcaat cgtagctgcg aggtgccaac aaggctaaat
 301 tctgcatccc tcaaacagcc ttatatcact cagaattatt ttccagtcgg tactgttgtg
 361 gaatatgagt gccgtccagg ttacagaaga gaaccttctc tatcaccaaa actaacttgc
 421 cttcagaatt taaaatggtc cacagcagtc gaattttgta aaagaaatc atgccctaat
 481 ccgggagaaa tacgaaatgg tcagattgat gtaccaggtg gcatattatt tggtgcaacc
 541 atctccttct catgtaacac agggtacaaa ttatttggct cgacttctag ttttttgtctt
 601 atttcaggca gctctgtcca gtggagtgac ccgttgccag agtgcagaga aatttattgt
 661 ccagcaccac cacaaattga caatggaata attcaagggg aacgtgacca ttatggatat
 721 agacagtctg taacgtatgc atgtaataaa ggattcacca tgattggaga gcactctatt
 781 tattgtactg tgaataatga tgaaggagag tggagtggcc caccacctga atgcagagga
 841 aaatctctaa cttccaaggt cccaccaaca gttcagaaac ctaccacagt aaatgttcca
 901 actacagaag tctcaccaac ttctcagaaa accaccacaa aaccaccac accaaatgct
 961 caagcaacac ggagtacacc tgtttccagg acaaccaagc attttcatga acaaccccca
1021 aataaaggaa gtggaaccac ttcaggtact acccgtcttc tatctgggca cacgtgtttc
1081 acgttgacag gtttgcttgg gacgctagta accatgggct tgctgactta gccaaagaag
1141 agttaagaag aaaatacaca caagtataca gactgttcct agtttcttag acttatctgc
1201 atattggata aaataaatgc aattgtgctc ttcatttagg atgctttcat tgtctttaag
1261 atgtgttagg aatgtcaaca gagcaaggag aaaaaaggca gtcctggaat cacattctta
1321 gcacacctgc gcctcttgaa aatagaacaa cttgcagaat tgagagtgat tcctttccta
1381 aaagtgtaag aaagcataga gatttgttcg tattaagaat gggatcacga ggaaaagaga
1441 aggaaagtga tttttttcca caagatctga aatgatattt ccacttataa aggaaataaa
1501 aaatgaaaaa cattatttgg atatcaaaag caaataaaaa cccaattcag tctcttctaa
1561 gcaaaattgc taagagagaa tgaccacatt ataaagtaat ctttggctaa ggcatttttca
1621 tctttccttc ggttggcaaa atattttaaa ggtaaaacat gctggtgaac cagggtgttg
1681 atggtgataa gggaggaata tagaatgaaa gactgaatct tcctttgttg cacaaataga
1741 gtttggaaaa agcctgtgaa aggtgtcttc tttgacttaa tgtctttaaa agtatccaga
1801 gatactacaa tattaacata agaaaagatt atatattatt tctgaatcga gatgtccata
1861 gtcaaatttg taaatcttat tcttttgtaa tatttatttta tatttattta tgacagtgaa
1921 cattctgatt ttacatgtaa aacaagaaaa gttgaagaag atatgtgaag aaaaatgtat
1981 ttttcctaaa tagaaataaa tgatcccatt ttttggt
```

FIG. 3A

PSVPAALPLLGELPRLLLLVLLCLPAVWGDCGLPPDVPNAQPAL

EGRTSFPEDTVITYKCEESFVKIPGEKDSVTCLKGMQWSDIEEFCNRSCEVPTRLNSA

SLKQPYITQNYFPVGTVVEYECRPGYRREPSLSPKLTCLQNLKWSTAVEFCKKKSCPN

PGEIRNGQIDVPGGILFGATISFSCNTGYKLFGSTSSFCLISGSSVQWSDPLPECREI

YCPAPPQIDNGIIQGERDHYGYRQSVTYACNKGFTMIGEHSIYCTVNNDEGEWSGPPP

ECRGKSLTSKVPPTVQKPTTVNVPTTEVSPTSQKTTTKTTTPNAQATRSTPVSRTTKH

FHETTPNKGSGTTSGTTRLLSGHTCFTLTGLLGTLVTMGLLT

```
   1 ccgctgggcg tagctgcgac tcggcggagt cccggcggcg cgtccttgtt ctaacccggc
  61 gcgccatgac cgtcgcgcgg ccgagcgtgc ccgcggcgct gcccctcctc ggggagctgc
 121 cccggctgct gctgctggtg ctgttgtgcc tgccggccgt gtggggtgac tgtggccttc
 181 ccccagatgt acctaatgcc cagccagctt tggaaggccg tacaagtttt cccgaggata
 241 ctgtaataac gtacaaatgt gaagaaagct ttgtgaaaat tcctggcgag aaggactcag
 301 tgatctgcct taagggcagt caatggtcag atattgaaga gttctgcaat cgtagctgcg
 361 aggtgccaac aaggctaaat tctgcatccc tcaaacagcc ttatatcact cagaattatt
 421 ttccagtcgg tactgttgtg gaatatgagt gccgtccagg ttacagaaga gaaccttctc
 481 tatccaccaaa actaacttgc cttcagaatt taaaatggtc cacagcagtc gaattttgta
 541 aaaagaaatc atgccctaat ccgggagaaa tacgaaatgg tcagattgat gtaccaggtg
 601 gcatattatt tggtgcaacc atctccttct catgtaacac agggtacaaa ttatttggct
 661 cgacttctag ttttttgtctt atttcaggca gctctgtcca gtggagtgac ccgttgccag
 721 agtgcagaga aatttattgt ccagccac cacaaattga caatggaata attcaagggg
 781 aacgtgacca ttatggatat agacagtctg taacgtatgc atgtaataaa ggattcacca
 841 tgattggaga gcactctatt tattgtactg taataatga tgaaggagag tggagtggcc
 901 caccacctga atgcagagga aaatctctaa cttccaaggt cccaccaaca gttcagaaac
 961 ctaccacagt aaatgttcca actacagaag tctcaccaac ttctcagaaa accaccacaa
1021 aaaccaccac accaaatgct caagcaacac ggagtacacc tgtttccagg acaaccaagc
1081 attttcatga acaaccccca aataaggaa gtggaaccac ttcaggtact acccgtcttc
1141 tatctggttc tcgtcctgtc acccaggctg gtatgcggtg gtgtgatcgt agctcactgc
1201 agtctcgaac tcctgggttc aagcgatcct tccacttcag cctcccaagt agctggtact
1261 acagggcaca cgtgtttcac gttgacaggt ttgcttggga cgctagtaac catgggcttg
1321 ctgacttagc caagaagag ttaagaagaa atacacaca agtatacaga ctgttcctag
1381 tttcttagac ttatctgcat attggataaa ataaatgcaa ttgtgctctt catttaggat
1441 gctttcattg tcttttaagat gtgttaggaa tgtcaacaga gcaaggagaa aaaaggcagt
1501 cctggaatca cattcttagc acacctacac ctcttgaaaa tagaacaact tgcagaattg
1561 agagtgattc ctttcctaaa agtgtaagaa agcatagaga tttgttcgta tttagaatgg
1621 gatcacgagg aaaagagaag gaaagtgatt tttttccaca agatctgtaa tgttatttcc
1681 acttataaag gaaataaaaa atgaaaaaca ttatttggat atcaaaagca aataaaaacc
1741 caattcagtc tcttctaagc aaaattgcta agagagatg aaccacatta taaagtaatc
1801 tttggctgta aggcattttc atctttcctt cgggttggca aaatatttta aggtaaaac
1861 atgctggtga accaggggtg ttgatggtga taggggagga atatagaatg aaagactgaa
1921 tcttcctttg ttgcacaaat agagtttgga aaaagcctgt gaaaggtgtc ttctttgact
1981 taatgtcttt aaaagtatcc agagatacta caatattaac ataagaaaag attatatatt
2041 atttctgaat cgagatgtcc atagtcaaat ttgtaaatct tattcttttg taatatttat
2101 ttatatttat ttatgacagt gaacattctg attttacatg taaaacaaga aagttgaag
2161 aagatatgtg aagaaaaatg tattttttcct aaatagaaat aaatgatccc attttttggt
```

B

MTVARPSVPAALPLLGELPRLLLLVLLCLPAVWGDCGLPPDVPN
AQPALEGRTSFPEDTVITYKCEESFVKIPGEKDSVICLKGSQWSDIEEFCNRSCEVPT
RLNSASLKQPYITQNYFPVGTVVEYECRPGYRREPSLSPKLTCLQNLKWSTAVEFCKK
KSCPNPGEIRNGQIDVPGGILFGATISFSCNTGYKLFGSTSSFCLISGSSVQWSDPLP
ECREIYCPAPPQIDNGIIQGERDHYGYRQSVTYACNKGFTMIGEHSIYCTVNNDEGEW
SGPPPECRGKSLTSKVPPTVQKPTTVNVPTTEVSPTSQKTTTKTTTPNAQATRSTPVS
RTTKHFHETTPNKGSGTTSGTTRLLSGHTCFTLTGLLGTLVTMGLLT

FIG. 4

CELLS FOR DETECTION OF ENTEROVIRUSES

This is a divisional of U.S. application Ser. No. 09/844,311, filed on Apr. 27, 2001 now U.S. Pat. No. 6,821,741.

FIELD OF THE INVENTION

The invention relates to cell lines which are useful for the rapid detection of enteroviruses. In particular, the invention relates to transgenic buffalo green monkey kidney cell lines which show increased sensitivity to infection by enteroviruses in single-cell type and mixed-cell type cultures, and which are permissive for infection by a broad spectrum of enteroviruses. The invention further relates to transgenic African green monkey kidney cells for detection of enteroviruses.

BACKGROUND OF THE INVENTION

Enteroviruses cause annual epidemics in North America in the period from late summer through early fall. While the majority of the infected individuals are asymptomatic, they are nonetheless capable of transmitting enteroviruses which cause a wide spectrum of diseases, including aseptic meningitis, encephalitis, paralysis, myocarditis, respiratory and gastrointestinal disorders, muscular disability, exanthema and reye's syndrome. In young children, enteroviruses are responsible for aseptic meningitis. Thus, early detection of infection with enteroviruses is critical for disease management.

Thus, to detect and/or isolate enteroviruses from clinical specimens, one approach employed by the prior art has been the use of cell cultures containing a single cell type which is susceptible to infection by enteroviruses, such as buffalo green monkey kidney (BGMK) cells and human lung mucoepidermoid carcinoma cells (NCI-H292, also referred to as H292). However, while BGMK cells are sensitive to some enteroviruses, such as Coxsackie B viruses, their sensitivity is poor to other enteroviruses, such as echoviruses. Similarly, the sensitivity of the H292 cells is variable to different enteroviruses.

Another approach which has been used by the prior art to detect and/or isolate a wider variety of enteroviruses from clinical specimens has employed using a combination of cells [such as primary monkey kidney cells, and cell lines of BGMK cells, human rhabdomyosarcoma (RD) cells, human epidermoid carcinoma (A-549) cells, MRC-5 cells, and others] which are susceptible to enteroviruses. However, even with this multi-cell type approach, and even when incorporating H292 or BGMK cells, the prior art's shell vial cultures and test tube cultures require from about 3 to about 5 day, respectively, to detect enteroviruses.

Thus, what is needed are cells with enhanced sensitivity for enteroviruses to allow rapid detection of enteroviruses, and for cells with a broader spectrum of susceptibility to enteroviruses to allow detection of several types of enteroviruses.

SUMMARY OF THE INVENTION

The invention provides cell lines which are useful for the rapid detection of enteroviruses. In particular, the invention provides transgenic African green monkey kidney cell lines and transgenic buffalo green monkey kidney cell lines. The transgenic buffalo green monkey kidney cell lines have increased sensitivity to infection by enteroviruses in single-cell type and mixed-cell type cultures compared to other cell types which are currently used for enterovirus detection. The transgenic buffalo green monkey kidney cell lines of the invention also are permissive to infection by a larger number of enteroviruses as compared to the cell type from which they were derived.

In particular, the invention provides a transgenic cell line designated BGMK-hDAF.

The invention further provides a cell line established from a transgenic cell line designated BGMK-hDAF, wherein the established cell line has a property selected from the group consisting of (a) increased sensitivity to one or more enteroviruses compared to buffalo green monkey kidney cell line, and (b) permissiveness to echovirus selected from the group consisting of echovirus-6 and echovirus-11. In one embodiment, the cell line has the sensitivity to enterovirus of cell line designated BGMK-hDAF. In another embodiment, the enterovirus is selected from the group consisting of polioviruses, Coxsackie A viruses, Coxsackie B viruses, echoviruses, and enterovirus types 68, 69, 70 and 71.

Also provided by the invention is a transgenic buffalo green monkey kidney cell line expressing human decay accelerating factor, wherein the cell line has a property selected from the group consisting of (a) increased sensitivity to one or more enteroviruses compared to buffalo green monkey kidney cell line, and (b) permissiveness to echovirus selected from the group consisting of echovirus-6 and echovirus-11. In one embodiment, the human decay accelerating factor is encoded by a sequence selected from SEQ ID NO:1 and SEQ ID NO:3. In another embodiment, the transgenic buffalo green monkey kidney cell line has the sensitivity to enterovirus of cell line designated as BGMK-hDAF. In yet another embodiment, the cell line is BGMK-hDAF. In a further embodiment, the enterovirus is selected from the group consisting of polioviruses, Coxsackie A viruses, Coxsackie B viruses, echoviruses, and enterovirus types 68, 69, 70 and 71. In a preferred embodiment, the echovirus is selected from the group consisting of echovirus-4, echovirus-6, echovirus-7, echovirus-9, echovirus-11, echovirus-30. In an alternative embodiment, the Coxsackie virus is selected from the group consisting of Coxsackie virus B1, Coxsackie virus B2, Coxsackie virus B4, Coxsackie virus B5, and Coxsackie virus A9.

The invention additionally provides a composition comprising a transgenic buffalo green monkey kidney cell expressing human decay accelerating factor, wherein the cell has a property selected from the group consisting of (a) increased sensitivity to one or more enterovirus compared to buffalo green monkey kidney cell line, and (b) permissiveness to echovirus selected from the group consisting of echovirus-6 and echovirus-11. In one embodiment, the composition further comprises a cell type other than the transgenic buffalo green monkey kidney cell line, and wherein the transgenic buffalo green monkey kidney cell and the cell type are in mixed-cell type culture. In another embodiment, the cell type is selected from the group consisting of CCD-13 Lu, CCD-8 Lu, CCD-14 Br, CCD-16 Lu, CCD-18 Lu, CCD-19 Lu, Hs888 Lu, MRC-9, CCD-25 Lu, WiDr, DLD-1, COLO205, HCT-15, SW 480, LOVO, SW403, SW48, SWI116, SW1463, SW837, SW948, SW1417, FHs74 Int, HCT-8, HCT-116, T84, NCI-H747, NCI-H508, LS123, CaCo-2, HT-29, SK-CO-1, HuTu 80, A253, A704, Hela, Hela, Hela53, L-132, Intestine, BHK-21, Hak, KB, Hep-2, Wish, Detroit 532, FL, Detroit 525, Detroit 529, Detroit 510, WI-38, WI-38 VA13, Citrullinemia, Spik (NBL-10), Detroit 539, Cridu Chat, W126 VA4, BeWo, SW-13, Detroit 548, Detroit 573, HT-1080, HG 261, C211, Amdur II, CHP 3 (M.W.), CHP 4 (W.W.), RD, HEL 299, Detroit 562, MRC-5, A-549, IMR-90, LS180, LS174T, BGMK, CV-1, and CV-1-hDAF. In a preferred embodiment, the cell type is selected from the group consisting of RD cells, H292 cells, A549 cells, MRC-5 cells, KB cells, and CaCo-2 cells. In a more preferred embodiment, the cell type is CaCo-2 cells.

The invention provides also a composition comprising a transgenic cell designated BGMK-hDAF. In one embodiment, the composition further comprises a cell type other than the BGMK-hDAF cell, and wherein the BGMK-hDAF cell and the cell type are in mixed-cell type culture. In an alternative embodiment, the cell type is selected from the group consisting of CCD-13 Lu, CCD-8 Lu, CCD-14 Br, CCD-16 Lu, CCD-18 Lu, CCD-19 Lu, Hs888 Lu, MRC-9, CCD-25 Lu, WiDr, DLD-1, COLO205, HCT-15, SW 480, LOVO, SW403, SW48, SWI-116, SW1463, SW837, SW948, SW1417, FHs74 Int, HCT-8, HCT-116, T84, NCI-H747, NCI-H508, LS123, CaCo-2, HT-29, SK-CO-1, HuTu 80, A253, A704, Hela, Hela, Hela53, L-132, Intestine, BHK-21, Hak, KB, Hep-2, Wish, Detroit 532, FL, Detroit 525, Detroit 529, Detroit 510, WI-38, WI-38 VA13, Citrullinemia, Spik (NBL-10), Detroit 539, Cridu Chat, W126 VA4, BeWo, SW-13, Detroit 548, Detroit 573, HT-1080, HG 261, C211, Amdur II, CHP 3 (M.W.), CHP 4 (W.W.), RD, HEL 299, Detroit 562, MRC-5, A-549, IMR-90, LS180, LS174T, BGMK, CV-1, and CV-1-hDAF. In another embodiment, the cell type is selected from the group consisting of RD cells, H292 cells, A549 cells, MRC-5 cells, KB cells, and CaCo-2 cells. In a more preferred embodiment, the cell type is CaCo-2 cells.

Also provided herein is composition comprising a cell established from a transgenic cell line designated BGMK-hDAF, wherein the established cell has a property selected from the group consisting of (a) increased sensitivity to one or more enteroviruses compared to buffalo green monkey kidney cell line, and (b) permissiveness to echovirus selected from the group consisting of echovirus-6 and echovirus-11. In one embodiment, the composition further comprises a cell type other than the established cell, and wherein the established cell and the cell type are in mixed-cell type culture. In another embodiment, the cell type is selected from the group consisting of CCD-13 Lu, CCD-8 Lu, CCD-14 Br, CCD-16 Lu, CCD-18 Lu, CCD-19 Lu, Hs888 Lu, MRC-9, CCD-25 Lu, WiDr, DLD-1, COLO205, HCT-15, SW 480, LOVO, SW403, SW48, SW116, SW1463, SW837, SW948, SW1417, FHs74 Int, HCT-8, HCT-116, T84, NCI-H747, NCI-H508, LS123, CaCo-2, HT-29, SK-CO-1, HuTu 80, A253, A704, Hela, Hela, Hela53, L-132, Intestine, BHK-21, Hak, KB, Hep-2, Wish, Detroit 532, FL, Detroit 525, Detroit 529, Detroit 510, WI-38, WI-38 VA13, Citrullinemia, Spik (NBL-10), Detroit 539, Cridu Chat, W126 VA4, BeWo, SW-13, Detroit 548, Detroit 573, HT-1080, HG 261, C211, Amdur II, CHP 3 (M.W.), CHP 4 (W.W.), RD, HEL 299, Detroit 562, MRC-5, A-549, IMR-90, LS180, LS174T, BGMK, CV-1, and CV-1-hDAF. In a preferred embodiment, the cell type is selected from the group consisting of RD cells, H292 cells, A549 cells, MRC-5 cells, KB cells, and CaCo-2 cells. In a more preferred embodiment, the cell type is CaCo-2 cells.

The invention additionally provides a method for detection of enterovirus in a sample, comprising: a) providing: i) a sample; and ii) a composition comprising a cell designated BGMK-hDAF; b) inoculating the cell with the sample to produce an inoculated cell; and c) observing the inoculated cell for the presence of the enterovirus. In one embodiment, the enterovirus is selected from the group consisting of polioviruses, Coxsackie A viruses, Coxsackie B viruses, echoviruses, and enterovirus types 68, 69, 70 and 71. In another embodiment, the composition further comprises a cell type other than the BGMK-hDAF cell, and wherein the BGMK-hDAF cell and the cell type are in mixed-cell type culture. In a further embodiment, the cell type is selected from the group consisting of CCD-13 Lu, CCD-8 Lu, CCD-14 Br, CCD-16 Lu, CCD-18 Lu, CCD-19 Lu, Hs888 Lu, MRC-9, CCD-25 Lu, WiDr, DLD-1, COL0205, HCT-15, SW 480, LOVO, SW403, SW48, SW116, SW1463, SW837, SW948, SW1417, FHs74 Int, HCT-8, HCT-116, T84, NCI-H747, NCI-H508, LS123, CaCo-2, HT-29, SK-CO-1, HuTu 80, A253, A704, Hela, Hela, Hela53, L-132, Intestine, BHK-21, Hak, KB, Hep-2, Wish, Detroit 532, FL, Detroit 525, Detroit 529, Detroit 510, WI-38, WI-38 VA13, Citrullinemia, Spik (NBL-10), Detroit 539, Cridu Chat, W126 VA4, BeWo, SW-13, Detroit 548, Detroit 573, HT-1080, HG 261, C211, Amdur II, CHP 3 (M.W.), CHP 4 (W.W.), RD, HEL 299, Detroit 562, MRC-5, A-549, IMR-90, LS180, LS174T, BGMK, CV-1, and CV-1-hDAF. In a preferred embodiment, the cell type is selected from the group consisting of RD cells, H292 cells, A549 cells, MRC-5 cells, KB cells, and CaCo-2 cells. In a more preferred embodiment, the cell type is CaCo-2 cells.

The invention also provides a transgenic cell line designated CV-1-hDAF.

Further provided is a cell line established from a transgenic cell line designated CV-1-hDAF, wherein the established cell line has a property selected from the group consisting of (a) increased sensitivity to one or more enteroviruses compared to CV-1 cell line, and (b) permissiveness to one or more enteroviruses to which CV-1 is not permissive. In one embodiment, the cell line has the sensitivity to enterovirus of cell line designated CV-1-hDAF. In another embodiment, the enterovirus is selected from the group consisting of polioviruses, Coxsackie A viruses, Coxsackie B viruses, echoviruses, and enterovirus types 68, 69, 70 and 71.

The invention also provides a transgenic African green monkey kidney cell line expressing human decay accelerating factor, wherein the cell line has a property selected from the group consisting of (a) increased sensitivity to one or more enteroviruses compared to CV-1 cell line, and (b) permissiveness to one or more enteroviruses to which CV-1 is not permissive. In a preferred embodiment, the human decay accelerating factor is encoded by a sequence selected from SEQ ID NO:1 and SEQ ID NO:3. In another preferred embodiment, the transgenic African green monkey kidney cell line has the sensitivity to enterovirus of cell line designated as CV-1-hDAF. In an alternative embodiment, the cell line is CV-1-hDAF. In yet another embodiment, the enterovirus is selected from the group consisting of polioviruses, Coxsackie A viruses, Coxsackie B viruses, echoviruses, and enterovirus types 68, 69, 70 and 71. In an additional embodiment, the echovirus is selected from the group consisting of echovirus-4, echovirus-6, echovirus-7, echovirus-9, echovirus-11, and echovirus-30. In a further embodiment, the Coxsackie virus is selected from the group consisting of Coxsackie virus B1, Coxsackie virus B2, Coxsackie virus B4, Coxsackie virus B5, and Coxsackie virus A9.

Also provided herein is a composition comprising a transgenic African green monkey kidney cell expressing human decay accelerating factor, wherein the cell has a property selected from the group consisting of (a) increased sensitivity to one or more enterovirus compared to CV-1 cell line, and (b) permissiveness to one or more enteroviruses to which CV-1 is not permissive. In one embodiment, the composition further comprises a cell type other than the transgenic African green monkey kidney cell line, and wherein the transgenic African green monkey kidney cell and the cell type are in mixed-cell type culture. In an alternative embodiment, the cell type is selected from the group consisting of CCD-13 Lu, CCD-8 Lu, CCD-14 Br, CCD-16 Lu, CCD-18 Lu, CCD-19 Lu, Hs888 Lu, MRC-9, CCD-25 Lu, WiDr, DLD-1, COLO205, HCT-15, SW 480, LOVO, SW403, SW48, SW116, SW1463, SW837, SW948, SW1417, FHs74 Int, HCT-8, HCT-116, T84, NCI-H747, NCI-H508, LS123, CaCo-2, HT-29, SK-CO-1, HuTu 80, A253, A704, Hela, Hela, Hela53, L-132, Intestine, BHK-21, Hak, KB, Hep-2, Wish, Detroit 532, FL, Detroit 525, Detroit 529, Detroit 510, WI-38, WI-38 VA13, Citrullinemia, Spik (NBL-10), Detroit 539, Cridu Chat, WI26 VA4, BeWo, SW-13, Detroit 548, Detroit 573, HT-1080, HG 261, C211, Amdur II, CHP 3 (M.W.), CHP 4 (W.W.), RD, HEL 299, Detroit 562, MRC-5, A-549, IMR-90, LS 180, LS174T, BGMK, BGMK-hDAF, and CV-1. In one preferred embodiment, the cell type is selected from the group consisting of RD cells, H292 cells, A549 cells, MRC-5 cells, KB cells, and CaCo-2 cells. In a more preferred embodiment, the cell type is CaCo-2 cells.

The invention further provides a composition comprising a transgenic cell designated CV-1-hDAF. In one embodiment, the composition further comprises a cell type other than the CV-1-hDAF cell, and wherein the CV-1-hDAF cell and the cell type are in mixed-cell type culture. In an alternative embodiment, the cell type is selected from the group consisting of CCD-13 Lu, CCD-8 Lu, CCD-14 Br, CCD-16 Lu, CCD-18 Lu, CCD-19 Lu, Hs888 Lu, MRC-9, CCD-25 Lu, WiDr, DLD-1, COLO205, HCT-15, SW 480, LOVO, SW403, SW48, SW116, SW1463, SW837, SW948, SW1417, FHs74 Int, HCT-8, HCT-116, T84, NCI-H747, NCI-H508, LS123, CaCo-2, HT-29, SK-CO-1, HuTu 80, A253, A704, Hela, Hela, Hela53, L-132, Intestine, BHK-21, Hak, KB, Hep-2, Wish, Detroit 532, FL, Detroit 525, Detroit 529, Detroit 510, WI-38, WI-38 VA13, Citrullinemia, Spik (NBL-10), Detroit 539, Cridu Chat, WI26 VA4, BeWo, SW-13, Detroit 548, Detroit 573, HT-1080, HG 261, C211, Amdur II, CHP 3 (M.W.), CHP 4 (W.W.), RD, HEL 299, Detroit 562, MRC-5, A-549, IMR-90, LS180, LS174T, BGMK, BGMK-hDAF, and CV-1. In a preferred embodiment, the cell type is selected from the group consisting of RD cells, H292 cells, A549 cells, MRC-5 cells, KB cells, and CaCo-2 cells. In a more preferred embodiment, the cell type is CaCo-2 cells.

Also provided by the invention is a composition comprising a cell established from a transgenic cell line designated CV-1-hDAF, wherein the established cell has a property selected from the group consisting of (a) increased sensitivity to one or more enteroviruses compared to CV-1 cell line, and (b) permissiveness to one or more enteroviruses to which CV-1 is not permissive. In one embodiment, the composition further comprises a cell type other than the established cell, and wherein the established cell and the cell type are in mixed-cell type culture. In another embodiment, the cell type is selected from the group consisting of CCD-13 Lu, CCD-8 Lu, CCD-14 Br, CCD-16 Lu, CCD-18 Lu, CCD-19 Lu, Hs888 Lu, MRC-9, CCD-25 Lu, WiDr, DLD-1, COLO205, HCT-15, SW 480, LOVO, SW403, SW48, SW116, SW1463, SW837, SW948, SW1417, FHs74 Int, HCT-8, HCT-116, T84, NCI-H747, NCI-H508, LS123, CaCo-2, HT-29, SK-CO-1, HuTu 80, A253, A704, Hela, Hela, Hela53, L-132, Intestine, BHK-21, Hak, KB, Hep-2, Wish, Detroit 532, FL, Detroit 525, Detroit 529, Detroit 510, WI-38, WI-38 VA13, Citrullinemia, Spik (NBL-10), Detroit 539, Cridu Chat, WI26 VA4, BeWo, SW-13, Detroit 548, Detroit 573, HT-1080, HG 261, C211, Amdur II, CHP 3 (M.W.), CHP 4 (W.W.), RD, HEL 299, Detroit 562, MRC-5, A-549, IMR-90, LS180, LS174T, BGMK, BGMK-hDAF, and CV-1. In a preferred embodiment, the cell type is selected from the group consisting of RD cells, H292 cells, A549 cells, MRC-5 cells, KB cells, and CaCo-2 cells. In a more preferred embodiment, the cell type is CaCo-2 cells.

The invention also provides a method for detection of enterovirus in a sample, comprising: a) providing: i) a sample; and ii) a composition comprising a cell designated CV-1-hDAF; b) inoculating the cell with the sample to produce an inoculated cell; and c) observing the inoculated cell for the presence of the enterovirus. In one embodiment, the enterovirus is selected from the group consisting of polioviruses, Coxsackie A viruses, Coxsackie B viruses, echoviruses, and enterovirus types 68, 69, 70 and 71. In another embodiment, the composition further comprises a cell type other than the CV-1-hDAF cell, and wherein the CV-1-hDAF cell and the cell type are in mixed-cell type culture. In an alternative embodiment, the cell type is selected from the group consisting of CCD-13 Lu, CCD-8 Lu, CCD-14 Br, CCD-16 Lu, CCD-18 Lu, CCD-19 Lu, Hs888 Lu, MRC-9, CCD-25 Lu, WiDr, DLD-1, COLO205, HCT-15, SW 480, LOVO, SW403, SW48, SWI16, SW1463, SW837, SW948, SW1417, FHs74 Int, HCT-8, HCT-116, T84, NCI-H747, NCI-H508, LS123, CaCo-2, HT-29, SK-CO-1, HuTu 80, A253, A704, Hela, Hela, Hela53, L-132, Intestine, BHK-21, Hak, KB, Hep-2, Wish, Detroit 532, FL, Detroit 525, Detroit 529, Detroit 510, WI-38, WI-38 VA13, Citrullinemia, Spik (NBL-10), Detroit 539, Cridu Chat, WI26 VA4, BeWo, SW-13, Detroit 548, Detroit 573, HT-1080, HG 261, C211, Amdur II, CHP 3 (M.W.), CHP 4 (W.W.), RD, HEL 299, Detroit 562, MRC-5, A-549, IMR-90, LS180, LS174T, BGMK, BGMK-hDAF, and CV-1. In a preferred embodiment, the cell type is selected from the group consisting of RD cells, H292 cells, A549 cells, MRC-5 cells, KB cells, and CaCo-2 cells. In a more preferred embodiment, the cell type is CaCo-2 cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows the nucleotide sequence (SEQ ID NO:1; GenBank Accession No. M15799) (A) which encodes the human decay accelerating factor polypeptide sequence (SEQ ID NO:2) (B).

FIG. 4 shows the nucleotide sequence (SEQ ID NO:3; GenBank Accession No. M30142) (A) which encodes the human decay accelerating factor (SEQ ID NO:4) (B).

DEFINITIONS

Figure 1:
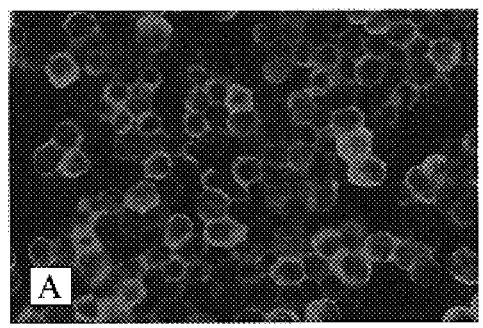
FIG. 1 shows immunofluorescence staining of hDAF protein on (A) BGMK-hDAF cells, (B) BGMK cells, (C)H292-hDAF cells, and (D) H292 cells.
Figure 1:
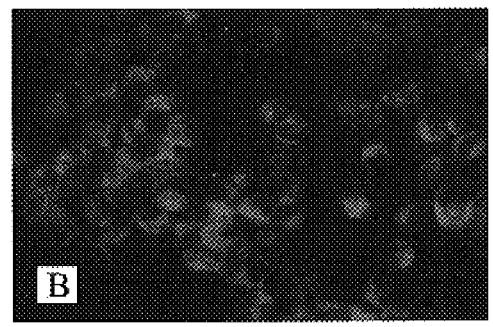
Figure 1:
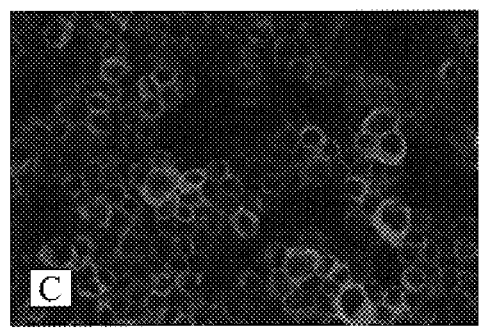
Figure 1:
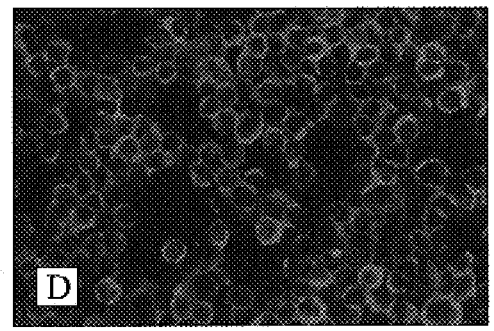

To facilitate understanding of the invention, a number of terms are defined below.

The terms "sample" and "specimen" in the present specification and claims are used in their broadest sense to include any composition that is obtained and/or derived from biological or environmental source, as well as sampling devices (e.g., swabs) which are brought into contact with biological or environmental samples. "Biological samples" include those obtained from an animal (including humans, domestic animals, as well as feral or wild animals, such as ungulates, bear, fish, lagamorphs, rodents, etc.), body fluids such as urine, blood, fecal matter, cerebrospinal fluid (CSF), semen, sputum, and saliva, as well as solid tissue. Also included are samples obtained from food products and food ingredients such as dairy items, vegetables, meat, meat by-products, and waste. "Environmental samples" include environmental material such as surface matter, soil, water, and industrial materials, as well as material obtained from food and dairy processing instruments, apparatus, equipment, disposable, and non-disposable items. These examples are not to be construed as limiting the sample types applicable to the present invention.

As used herein, the term "cell type," refers to any cell, regardless of its source or characteristics.

As used herein, the term "microorganism" refers to any organism of microscopic or ultramicroscopic size including, but not limited to, viruses, bacteria, and protozoa.

As used herein, the term "culture" refers to a composition, whether liquid, gel, or solid, which contains one or more microorganisms and/or one or more cells. A culture of organisms and/or cells can be pure or mixed. For example, a "pure culture" of an organism as used herein refers to a culture in which the organisms present are of only one strain of a single species of a particular genus. This is in contrast to a "mixed culture" of organisms which refers to a culture in which more than one strain of a single genus and/or species of microorganism is present.

As used herein, the terms "culture media," and "cell culture media," refer to media that are suitable to support maintenance and/or growth of cells in vitro (i.e., cell cultures).

A "primary cell" is a cell which is directly obtained from a tissue or organ of an animal whether or not the cell is in culture.

A "cultured cell" is a cell which has been maintained and/or propagated in vitro. Cultured cells include primary cultured cells and cell lines.

"Primary cultured cells" are primary cells which are in in vitro culture and which preferably, though not necessarily, are capable of undergoing ten or fewer passages in in vitro culture before senescence and/or cessation of proliferation.

The terms "cell line" and "immortalized cell" refer to a cell which is capable of a greater number of cell divisions in vitro before cessation of proliferation and/or senescence as compared to a primary cell from the same source. A cell line includes, but does not require, that the cells be capable of an infinite number of cell divisions in culture. The number of cell divisions may be determined by the number of times a cell population may be passaged (i.e., subcultured) in in vitro culture. Passaging of cells is accomplished by methods known in the art. Briefly, a confluent or subconfluent population of cells which is adhered to a solid substrate (e.g., plastic Petri dish) is released from the substrate (e.g., by enzymatic digestion), and a proportion (e.g., 10%) of the released cells is seeded onto a fresh substrate. The cells are allowed to adhere to the substrate, and to proliferate in the presence of appropriate culture medium. The ability of adhered cells to proliferate may be determined visually by observing increased coverage of the solid substrate over a period of time by the adhered cells. Alternatively, proliferation of adhered cells may be determined by maintaining the initially adhered cells on the solid support over a period of time, removing and counting the adhered cells and observing an increase in the number of maintained adhered cells as compared to the number of initially adhered cells.

Cell lines may be generated spontaneously or by transformation. A "spontaneous cell line" is a cell line which arises during routine culture of cells. A "transformed cell line" refers to a cell line which is generated by the introduction of a "transgene" comprising nucleic acid (usually DNA) into a primary cell or into a finite cell line by way of human intervention Cell lines include, but are not limited to, finite cell lines and continuous cell lines. As used herein, the term "finite cell line" refers to a cell line which is capable of a limited number (from about 1 to about 50, more preferably from about 1 to about 40, and most preferably from about 1 to about 20) of cell divisions prior to senescence.

The term "continuous cell line" refer to a cell line which is capable of more than about 50 (and more preferably, an infinite number of) cell divisions. A continuous cell line generally, although not necessarily, also has the general characteristics of a reduced cell size, higher growth rate, higher cloning efficiency, increased tumorigenicity, and/or a variable chromosomal complement as compared to the finite cell line or primary cultured cells from which it is derived.

The term "transgene" as used herein refers to any nucleic acid sequence which is introduced into the cell by experimental manipulations. A transgene may be an "endogenous DNA sequence" or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "nucleotide sequence of interest" refers to any nucleotide sequence, the manipulation of which may be deemed desirable for any reason, by one of ordinary skill in the art. Nucleotide sequences of interest include, but are not limited to, coding sequences of structural genes (e.g., reporter genes, selection marker genes, oncogenes, drug resistance genes, growth factors, etc.), and non-coding regulatory sequences which dfo not encode an mRNA or protein product, (e.g., promoter sequence, polyadenylation sequence, termination sequence, enhancer sequence, etc.).

The terms "enterovirus" and "enteroviruses" refer to RNA viruses which are of the piconarviridae family as previosuly described [Fieldes Virology (1996), 3rd Edition, Publ: Lippincott S. Raben, Chapter 22]. Enteroviruses have sense RNA and non-enveloped virus particles. Enteroviruses include, without limitation, polioviruses, Coxsackie A viruses, Coxsackie B viruses, echoviruses, and enterovirus types 68, 69, 70 and 71. Polioviruses are exemplified, but not limited to poliovirus types 1, 2, and 3. Coxsackie A viruses include, without limitation, Coxsackie virus types A1, A2, A3, A4, A5, A6, A7, A8, A9, A10, A11, A12, A13, A14, A15, A16, A17, A18, A19, A20, A21, and A24. Coxsackie B viruses are exemplified by Coxsackie virus types B1, B2, B3, B4, B5, and B6. Echoviruses include, by way of example, echovirus types 1, 2, 3, 4, 5, 6, 7, 8, 9, 11, 12, 13, 14, 15, 16, 17, 18, 19, 20, 21, 22, 23, 24, 25, 26, 27, 29, 30, 31, 32, 33, and 34.

DESCRIPTION OF THE INVENTION

The invention provides cell lines which are useful for the rapid detection of enteroviruses. In particular, the invention provides transgenic African green monkey kidney cell lines and transgenic buffalo green monkey kidney cell lines. The transgenic buffalo green monkey kidney cell lines of the invention have increased sensitivity to infection by enteroviruses in single-cell type and mixed-cell type cultures compared to other cell types which are currently used for enterovirus detection. The transgenic buffalo green monkey kidney cell lines of the invention also are permissive to infection by a larger number of enteroviruses as compared to the cell type from which they were derived.

More particularly, the invention provides transgenic African green monkey kidney (CV-1) cells and transgenic buffalo green monkey kidney (BGMK) cells which express the human decay accelerating factor (hDAF). The expanded enterovirus spectrum and increased susceptibility for the detection of enteroviruses, and the additional boost in sensitivity makes the invention's transgenic buffalo green monkey kidney cells a valuable tool for the rapid detection and/or isolation of enteroviruses in clinical laboratories. In particular, the invention's transgenic buffalo green monkey kidney cell lines allow detection of a broad spectrum of enteroviruses within 1 to 2 days. This is in contrast to the 4 to 5 days which are currently required for enterovirus detection using the prior art's single-cell type and mixed-cell type compositions.

For example, data provided herein demonstrates that the exemplary BGMK-hDAF cells of the invention have enhanced sensitivity to enteroviruses compared to BGMK cells. In particular, compared to BGMK cells, the invention's exemplary BGMK-hDAF cells were at least 10 times more sensitive in detecting echoviruses-4 and echovirus-9 at day 1, at least 15-20 times more sensitive in detecting echovirus-7 and echovirus-30 at day 3 (Example 2, Table 2), and at least 15–20 more sensitive in detecting Coxsackie virus A9, B1, and B5 at day 1 (Example 2, Table 3). Moreover, the invention's exemplary BGMK-hDAF cells were more sensitive to enteroviruses in clinical samples than BGMK cells as demonstrated by the detection of enteroviruses in 33 clinical samples as compared to in only 21 clinical samples by BGMK-hDAF and BGMK, respectively (Example 7, Table 10).

Not only were the invention's exemplary BGMK-hDAF capable of detecting a lower enterovirus titer than BGMK cells, but they also detected enteroviruses at an earlier time following infection than did BGMK cells. For example, the invention's exemplary BGMK-hDAF cells detected a larger number of enterovirus-positive clinical samples at day 1 following infection than the number detected by BGMK cells (Example 3, Table 4; Example 4, Table 5).

Importantly, both single-cell type and mixed-cell type cultures containing the invention's exemplary BGMK-hDAF cells were more sensitive to enteroviruses in clinical samples than any other commercially available single-cell type or mixed-cell type cultures tested, respectively (Example 7, Table 9). For example, single cell-type culture of the invention's exemplary BGMK-hDAF cells were more sensitive to enteroviruses in clinical samples than any other single-cell type culture tested (including BGMK cells, MRC-5 cells, primary rhesus monkey kidney cells, and Caco-2 cells) and mixed-cell type culture tested (including mixtures of RD and H292 cells; of BGMK and A549 cells; of RD, H292, BGMK and A549 cells; and of MRC-5 and primary rhesus monkey kidney cells). Similarity, mixed-cell type cultures containing Caco-2 cells and the invention's BGMk-hDAF cells were more sensitive to enteroviruses in clinical samples than any mixed-cell type culture tested (including mixtures of RD and H292 cells; of BGMK and A549 cells; of RD, H292, BGMK and A549 cells; and of MRC-5 and primary rhesus monkey kidney cells).

In addition to enhanced sensitivity to enteroviruses, the invention's exemplary BGMK-hDAF cells also were susceptible to a larger number of enteroviruses than BGMK cells. For example, data presented herein demonstrates that, whereas BGMK cells were incapable of detecting echovirus-6 or echovirus-11, the invention's exemplary BGMK-hDAF cells detected both echovirus-6 or echovirus-11 (Example 2, Table 2).

The properties and advantages of the invention's transgenic BGMK cells were surprising in view of contrary data disclosed herein when using transgenic H292 cells. In particular, data disclosed herein demonstrates that, whereas transfection of BGMK cells with vectors that express human decay accelerating factor increased both the sensitivity and permissiveness of BGMK cells to enteroviruses, in contrast, no increase in sensitivity to enteroviruses was observed when the same vectors were used to transfect H292 cells.

The invention is further described under (A) Transgenic African Green Monkey Kidney Cells And Buffalo Green Monkey Kidney Cells Which Express Human Decay Accelerating Factor, (B) Cultures Containing Transgenic Cells Of The Invention, and (C) Detection Of Enteroviruses In Cell Cultures.

A. Transgenic African Green Monkey Kidney Cells and Transgenic Buffalo Green Monkey Kidney Cells Which Express Human Decay Accelerating Factor The invention provides transgenic African green monkey kidney (CV-1) cells and transgenic buffalo green monkey (BGMK) cells which express the human decay accelerating factor (hDAF). The decay accelerating factor (DAF) (CD55) is a 70 kDa glycosylphosphatidylinositol (GPI) anchored glycoprotein involved in the regulation of complement activation and in cell signalling. It was the inventors' consideration that DAF is involved in the entry of echoviruses 3, 6, 7, 11, 12, 13, 19, 21, 24, 25, 29, 30, 33, Coxsackie viruses A21, B1, B3, B5, and enterovirus 70 into cells. For example, Bergelson et al. and others [Bergelson et al. (1994) Proc. Natl. Acad. Sci. 91:6245-6248; Bergelson et al. (1995) J. Virol. 69:1903-1906; Clarkson et al. (1995) J. Virol. 69:5497-5501] demonstrated that Chinese hamster ovary (CHO) cells which express decay accelerating factor (CD55) can bind echoviruses type 3, 6, 7, 12, 13, 21, 29, 33. Virus binding was also demonstrated to be blocked by anti-DAF monoclonal antibody. Powell et al. [Powell et al. (1998) J.

Gen. Virol. 79:1707-1713; Powell et al. (1999) J. Gen. Virol. 80:3145-3152] showed that anti-DAF monoclonal antibody can block echoviruses type 11, 19, 24, 25, 30 from binding to rhabdomyosarcoma (RD) cells. In addition to echoviruses, Shafren et al. [Shafren et al. (1995) J. Virol. 69:3873-3877; Shafren et al. (1997) J. Virol. 71:4736-4743] reported that Coxsackie virus A21 also binds to DAF of HEp-2 and HeLa B cells. Martino et al. [Martino et al. (1998) Virol. 244:302-314] and Shafren et al., [Shafren et al. (1995) supra] also reported that the binding of Coxsackie viruses B1, B3, B5 to HeLa cells could be blocked by anti-DAF monoclonal antibody. Yet another report by Karnauchow et al. [Karnauchow et al. (1996) J. Virol. 70:5143-5152; Karnauchow et al. (1998) J. Virol. 72:9380-9383] demonstrated that enterovirus 70 can bind to HeLa cells but that this binding may be blocked by anti-DAF monoclonal antibody. Stable expression of DAF in murine NIH3T3 cells has been shown to support the replication of enterovirus 70, whereas NIH3T3 cells which do not express DAF could not support such replication.

The invention's cells are exemplified by the transgenic African green monkey kidney cell line designated herein as CV-1-hDAF, and by the transgenic buffalo green monkey kidney cell line designated herein as BGMK-hDAF. The term "transgenic cell line designated as BGMK-hDAF" as used herein refers to any transgenic green monkey kidney cell line expressing human decay accelerating factor. The term "transgenic cell line designated as CV-1-hDAF" as used herein refers to any transgenic African green monkey kidney cell line expressing human decay accelerating factor. The cell lines CV-1-hDAF and BGMK-hDAF will be deposited at the American Type Culture Collection, 12301 Parklawn Drive, Rockville, Md.

However, the invention is not limited to the transgenic cell line BGMk-hDAF. Rather, the invention contemplates within its scope any transgenic buffalo green monkey kidney cell line which expresses human decay accelerating factor. Also, the invention is not limited to the transgenic cell line CV-1-hDAF, but includes within its scope any transgenic African green monkey kidney cell line which expresses human decay accelerating factor.

The terms "transgenic" and "genetically engineered" when made in reference to a buffalo green monkey kidney cell line refer to a buffalo green monkey kidney (BGMK) cell line (such as the BGMK cell line purchased from Diagnostic Hybrids, Inc., catalog # 53) that contains a transgene which encodes human decay accelerating factor, or whose genome has been altered by the introduction of such a transgene by way of human intervention, such as by the methods described herein. The terms "transgenic" and "genetically engineered" when made in reference to an African green monkey kidney cell line refer to an African green monkey kidney (CV-1) cell line (such as the CV-1 cell line, ATCC # CCL 70) that contains a transgene which encodes human decay accelerating factor, or whose genome has been altered by the introduction of such a transgene by way of human intervention, such as by the methods described herein.

The terms "human decay accelerating factor," "human decay accelerating factor amino acid sequence," "human decay accelerating factor polypeptide," refer to the polypeptide sequence listed as SEQ ID NO:2 (FIG. 3) and/or SEQ ID NO:4 (FIG. 4). It is also expressly contemplated that the term "human decay accelerating factor" includes variants of SEQ ID NO:2 and/or SEQ ID NO:4 which have the biological function of SEQ ID NO:2 and/or SEQ ID NO:4, respectively.

A "variant" of SEQ ID NO:2 and/or SEQ ID NO:4 as used herein is defined as an amino acid sequence which differs by insertion, deletion, and/or conservative substitution of one or more amino acids from SEQ ID NO:2 and/or SEQ ID NO:4, respectively. The term "conservative substitution" of an amino acid refers to the replacement of that amino acid with another amino acid which has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains which may be conservatively substituted one for the other include phenylalanine, tyrosine, and tryptophan. Cysteine and methionine are sulphur-containing amino acids which may be conservatively substituted one for the other. Also, asparagine may be conservatively substituted for glutamine, and vice versa, since both amino acids are amides of dicarboxylic amino acids. In addition, aspartic acid (aspartate) my be conservatively substituted for glutamic acid (glutamate) as both are acidic, charged (hydrophilic) amino acids. Also, lysine, arginine, and histidine my be conservatively substituted one for the other since each is a basic, charged (hydrophilic) amino acid. Guidance in determining which and how many amino acid residues may be substituted, inserted or deleted without abolishing biological or immunological activity may be found using computer programs well known in the art, for example, DNAStar software.

Variants of SEQ ID NO:2 and SEQ ID NO:4 are exemplified, but not limited to the polypeptide sequence of SEQ ID NO:2 in which one of the following conservative substitutions are made: Ala5 (i.e., Ala at position 5) is changed to Gly, Ala6 is changed to Val, Leu7 is changed to Ala, Leu10 is changed to Gly, Leu13 is changed to Ile, Leu21 is changed to Ser, Cys23 is changed to Met, Val27 is changed to Gly, Leu44 is changed to Thr, Thr48 is changed to Gly, Ser49 is changed to Gly, Val55 is changed to Ala, Ile56 is changed to Gly, Tyr58 is changed to Phe, Cys60 is changed to Met, Phe64 is changed to Tyr, Val74 is changed to Leu, Cys76 is changed to Met, Ser83 is changed to Ala, Ile85 is changed to Ala, Ala102 is changed to Thr, Ile109 is changed to Val, Thr110 is changed to Ala, Val 116 is changed to Ile, Val120 is changed to Ser, Thr148 is changed to Val, Ala149 is changed to Gly, Val171 is changed to Ser, Leu176 is changed to Ser, Trp177 is changed to Trp, Ser 182 is changed to Val, Leu200 is changed to Val, Ser202 is changed to Leu, Leu212 is changed to Gly, Tyr219 is changed to Trp, Cys220 is changed to Met, Ala222 is changed to Val, Ile231 is changed to Leu, Ile255 is changed to Thr, Ser259 is changed to Thr, Ile260 is changed to Ser, Lys286 is changed to Arg, Val297 is changed to Thr, Thr302 is changed to Leu, Thr311 is changed to Ser, Ala320 is changed to Ile, Ser329 is changed to Thr, Phe335 is changed to Trp, Lys342 is changed to Arg, Leu362 is changed to Ile, and Leu375 is changed to Thr.

Variants of SEQ ID NO:2 and SEQ ID NO:4 which include conservative substitutions of two amino acid are exemplified by the polypeptide sequence of SEQ ID NO:2 in which Ala6 is changed to Val and Leu13 is changed to Ile; Cys23 is changed to Met and Val27 is changed to Gly; Val55 is changed to Ala and Val116 is changed to Ile; Tyr58 is changed to Phe and Ile85 is changed to Ala; Cys60 is changed to Met and Ile85 is changed to Ala; Val74 is changed to Leu and Thr311 is changed to Ser; Ala102 is changed to Thr and Lys342 is changed to Arg; Thr110 is changed to Ala and Cys220 is changed to Met; Ser 182 is changed to Val and Thr302 is changed to Leu; and Leu212 is changed to Gly and Leu375 is changed to Thr. Variants of SEQ ID NO:2 and SEQ ID NO:4 which include conservative substitutions of three or more amino acid are exemplified by the polypeptide sequence of SEQ ID NO:2 in which Ala5 is changed to Gly, Ala6 is changed to Val and Leu7 is changed to Ala; Leu10 is changed to Gly, Ser49 is changed to Gly, and Phe64 is changed to Tyr; Val27 is changed to Gly, Ala149 is changed to Gly, Val171 is changed to Ser, and Tyr219 is changed to Trp; Leu44 is changed to Thr, Val116 is changed to Ile, Val171 is changed to Ser, Ala222 is changed to Val, and Ile260 is changed to Ser; Val74 is changed to Leu, Thr148 is changed to Val, Ala149 is changed to Gly, Trp177 is changed to Trp, Leu212 is changed to Gly, Ala222 is changed to Val, Ile231 is changed to Leu, and Lys342 is changed to Arg; and Val116 is changed to Ile, Ser 182 is changed to Val, Ser202 is changed to Leu, Tyr219 is changed to Trp, Ala222 is changed to Val, Ile255 is changed to Thr, Lys286 is changed to Arg, Ala320 is changed to Ile, Phe335 is changed to Trp, Leu362 is changed to Ile, and Leu375 is changed to Thr.

The term "has the biological activity of SEQ ID NO:2 and/or SEQ ID NO:4," when made in reference to the biological activity of a variant of SEQ ID NO:2 and/or SEQ ID NO:4, refers to a quantity of binding of enterovirus to the variant of SEQ ID NO:2 and/or SEQ ID NO:4 which is preferably greater than 1%, more preferably from 2% to 500%, more preferably from 2% to 200%, yet more preferably from 2% to 100%, and most preferably from 50% to 100%, as compared to the quantity of binding of the same enterovirus to SEQ ID NO:2 and/or SEQ ID NO:4, respectively. The quantity of binding of an enterovirus to SEQ ID NO:2, SEQ ID NO:4, and/or variants thereof may be determined using methods known in the art such as those disclosed by Powell et al (1998), supra. Briefly, $10^7$ cells which express SEQ ID NO:2, SEQ ID NO:4, and/or variants thereof are incubated with approximately $10^4$ c.p.m. of $^{35}$-S-labeled enterovirus for 1 hour on ice. The cells are harvested by centrifugation, unbound radioactivity is removed by washing with PBS, and the radioactivity bound to cells is quantified by scintillation counting. The detection of a quantity of cell-bound radioactivity in the cells which express a variant of SEQ ID NO:2 and/or SEQ ID NO:4 which is greater than 1%, more preferably from 2% to 500%, more preferably from 2% to 200%, yet more preferably from 2% to 100%, and most preferably from 50% to 100%, as compared to the quantity of cell-bound radioactivity in control cells which express SEQ ID NO:2 and SEQ ID NO:4, respectively, means that the variant has the biological activity as SEQ ID NO:2 and/or SEQ ID NO:4, respectively.

As used herein, the terms "nucleic acid molecule encoding," "DNA sequence encoding," and "DNA encoding" human decay accelerating factor and grammatical equivalents thereof, refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence of human decay accelerating factor. In one preferred embodiment, the transgene comprises the nucleotide sequence (SEQ ID NO:1; GenBank Accession No. M15799; FIG. 3) which encodes the human decay accelerating factor (SEQ ID NO:2). In an alternative preferred embodiment, the transgene comprises the nucleotide sequence (SEQ ID NO:3; GenBank Accession No. M30142; FIG. 4) which encodes the human decay accelerating factor (SEQ ID NO:4).

While not required, in one embodiment, it may be desirable that the transgene further include a sequence encoding a selectable marker. The term "selectable marker" as used herein refers to nucleotide sequence which encodes an enzymatic activity that confers resistance to a compound (e.g., antibiotic or drug) upon the cell in which the selectable marker is expressed. Selectable markers may be "positive"; i.e., genes which encode an enzymatic activity which can be detected in any cell or cell line. Examples of dominant selectable markers include, but are not limited to, (1) the bacterial aminoglycoside 3' phosphotransferase gene (also referred to as the neo gene) which confers resistance to the drug G418 in cells, (2) the bacterial hygromycin G phosphotransferase (hyg) gene which confers resistance to the antibiotic hygromycin, and (3) the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Selectable markers may be "negative"; negative selectable markers encode an enzymatic activity whose expression is cytotoxic to the cell when grown in an appropriate selective medium. For example, the HSV-tk gene and the dt gene are commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme. Similarly, the expression of the dt gene selects against cells capable of expressing the Diphtheria toxin. In one preferred embodiment, the selectable marker gene used is the neo gene in plasmid pcDNA3 (Invitrogen). Cells which incorporated this transgene were selected by exposure to Geneticin (G418) (Gibco-BRL Inc.) (Examples 1 and 8).

Vectors (e.g., plasmids, linear DNA, viruses, etc.) which contain a nucleotide sequence that encodes the human decay accelerating factor may be introduced into cells using techniques well known in the art. The term "introducing" a nucleic acid sequence into a cell refers to the introduction of the nucleic acid sequence into a target cell to produce a transformed cell. Methods of introducing nucleic acid sequences into cells are well known in the art. For example, where the nucleic acid sequence is a plasmid or naked piece of linear DNA, the sequence may be "transfected" into the cell using, for example, calcium phosphate-DNA co-precipitation, DEAE-dextran-mediated transfection, polybrene-mediated transfection, electroporation, microinjection, liposome fusion, lipofection, protoplast fusion, and biolistics. Alternatively, where the nucleic acid sequence is encapsidated into a viral particle, the sequence may be introduced into a cell by "infecting" the cell with the virus. In a preferred embodiment, the vector is a plasmid.

Transformation of a cell may be stable or transient. The terms "transient transformation" and "transiently transformed" refer to the introduction of one or more nucleotide sequences of interest into a cell in the absence of integration of the nucleotide sequence of interest into the host cell's genome. Transient transformation may be detected by, for example, enzyme-linked immunosorbent assay (ELISA) which detects the presence of a polypeptide encoded by one or more of the nucleotide sequences of interest. Alternatively, transient transformation may be detected by detecting the activity of the protein (e.g., β-glucuronidase) encoded by the nucleotide sequence of interest. The term "transient transformant" refer to a cell which has transiently incorporated one or more nucleotide sequences of interest.

In contrast, the terms "stable transformation" and "stably transformed" refer to the introduction and integration of one or more nucleotide sequence of interest into the genome of a cell. Thus, a "stable transformant" is distinguished from a transient transformant in that, whereas genomic DNA from the stable transformant contains one or more nucleotide sequences of interest, genomic DNA from the transient transformant does not contain the nucleotide sequence of interest. Stable transformation of a cell may be detected by Southern blot hybridization of genomic DNA of the transformed cell using nucleic acid sequences which are capable of binding to the nucleotide sequence of interest. Alternatively, stable transformation of a cell may also be detected by the polymerase chain reaction of genomic DNA of the transformed cell to amplify the nucleotide sequence of interest. In a preferred embodiment, transformation is stable as demonstrated by expression of hDAF by the exemplary transgenic cell line BGMK-hDAF after 50 passages (Example 1).

In one preferred embodiment, the transgenic BGMK cells and the transgenic CV-1 cells provided herein express human decay accelerating factor. The term "express human decay accelerating factor" when made in reference to a cell means that the cell contains a quantity of soluble or membrane-bound human decay acceleration factor which is detectable by, for example, an Enzyme Linked Immunosorbent Assay (ELISA) as described herein.

Expression of the hDAF protein may be determined directly or indirectly using methods known in the art. For example, indirect detection my be achieved by immunofluorescence assays such as those disclosed herein, wherein the transfected cells are incubated with anti-hDAF monoclonal antibody (PharMingen. San Diego, Calif.) and FITC-conjugated goat anti-mouse IgG as a second antibody, followed by observation of immunofluorescence under the microscope.

Alternatively, expression of the hDAF protein may be determined indirectly by detecting the activity of a reporter protein which is encoded by a reporter gene (e.g., the uid A gene) that is operably linked to the gene which encodes the hDAF protein. The term "reporter gene" refers to a gene which encodes a reporter molecule (e.g., RNA, polypeptide, etc.) which is detectable in any detection system, including, but not limited to enzyme (e.g., ELISA, as well as enzyme-based histochemical assays), fluorescent, radioactive, and luminescent systems. Exemplary reporter genes include, for example, β-glucuronidase gene, green fluorescent protein gene, E. coli β-galactosidase gene, human placental alkaline phosphatase gene, and chloramphenicol acetyltransferase gene. It is not intended that the present invention be limited to any particular detection system or label.

In a preferred embodiment, the number of transformed BGMK cells (or of transformed CV-1 cells) which express hDAF may be enriched relative to BGMK cells (or CV-1 cells) which do not express hDAF using methods known in the art, such as those disclosed herein. For example, cells may be labeled with anti-hDAF monoclonal antibody and FITC conjugated goat anti-mouse IgG (Chemicon), sorted by fluorescence activated cell sorting (FACS) to select for cells of relatively high hDAF expression, and cloned by limiting dilution.

While the invention is illustrated using the exemplary transgenic BGMK-hDAF cells deposited as ATCC # PTA-4594, and by the exemplary transgenic CV-1-hDAF cells, it is expressly contemplated that the invention is not limited to these particular cell types. Rather, the invention contemplates within its scope any cell line which is established from the transgenic cell line designated herein as BGMK-hDAF cells deposited as ATCC # PTA-4594. Further, the invention also contemplates within its scope any cell line which is established from the transgenic cell line designated herein as CV-1-hDAF cells.

The term "established from" when made in reference to a cell line in relation either to the transgenic cell line designated BGMK-hDAF deposited as ATCC # PTA-4594, or to the transgenic cell line designated CV-1-hDAF, refers to a cell line which has been obtained (e.g., isolated, purified, etc.) either from the transgenic cell line designated BGMK-hDAF which will be deposited as ATCC # PTA-4594, or from the transgenic cell line designated CV-1-hDAF, respectively, using any manipulation, such as, without limitation, infection with virus, transfection with DNA sequences, treatment and/or mutagenesis using for example chemicals, radiation, etc., selection of any cell that is contained in the transgenic cell line designated BGMK-hDAF, etc. For example, a cell line established from the transgenic cell line designated BGMK-hDAF includes BGMK-hDAF cells which have been treated with chemical compounds [e.g., N-ethyl-N-nitrosurea (ENU), methylnitrosourea (MNU), procarbazine hydrochloride (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6MP), mitomycin-C (MMC), procarbazine (PRC), N-methyl-N'-nitro-N-nitrosoguanidine (MNNG), $^3H_2O$, and urethane (UR)], and electromagnetic radiation [e.g., X-ray radiation, gamma-radiation, ultraviolet light].

The exemplary transgenic BGMK-hDAF cells of the invention show the surprising property of being susceptible to, and permissive for, infection by echovirus-6 and echovirus-11. This is in contrast to BGMK cells from which the invention's transgenic cells were derived, and which were not permissive to either echovirus-6 and echovirus-11.

The term "susceptible" as used herein in reference to a cell describes the ability of a permissive or non-permissive host cell to adsorb and be penetrated by a virus. A cell line may be susceptible without being permissive in that it can be penetrated by a virus in the absence of viral proliferation and/or release of virions from the cell. A permissive cell line however must be susceptible. Susceptibility of a cell to a virus may be determined by methods known in the art such as detecting the presence of viral proteins using electrophoretic analysis (i.e., SDS-PAGE) of protein extracts prepared from the infected cell cultures.

The terms "permissive" and "permissiveness" as used herein describe the sequence of interactive events between a virus and its putative host cell. The process begins with viral adsorption to the host cell surface and ends with release of infectious virions. A cell is "permissive" (i.e., shows "permissiveness") if it is capable of supporting viral proliferation as determined by, for example, production of viral nucleic acid sequences and/or of viral peptide sequences, regardless of whether the viral nucleic acid sequences and viral peptide sequences are assembled into a virion. While not required, in a preferred embodiment, a cell is permissive if it generates virions and/or releases the virions contained therein. Many methods are available for the determination of the permissiveness of a given cell line. For example, the proliferation of a particular virus in a host cell line may be measured by the production of various viral markers including viral proteins, viral nucleic acid (including both RNA and DNA) and the progeny virus. The presence of viral proteins may be determined using electrophoretic analysis (i.e., SDS-PAGE)

of protein extracts prepared from the infected cell cultures. Viral DNA or RNA may be quantitated using nucleic acid hybridization assays. Production of progeny virus may be determined by observation of a cytopathic effect. The invention is not limited to the specific quantity of proliferation of a virus.

The term "not permissive" means that the cell is not capable of supporting viral proliferation as determined by, for example, production of viral nucleic acid sequences and/or of viral peptide sequences, and/or assembly of viral nucleic acid sequences and viral peptide sequences into a virion.

The phrase "viral proliferation" as used herein describes the spread or passage of infectious virus from a permissive cell type to additional cells of either a permissive or susceptible character.

The terms "cytopathic effect" or "CPE" as used herein describe changes in cellular structure (i.e., a pathologic effect). Common cytopathic effects include cell destruction, syncytia (i.e., fused giant cells) formation, cell rounding, vacuole formation, and formation of inclusion bodies. CPE results from actions of a virus on permissive cells that negatively affect the ability of the permissive cellular host to preform its required functions to remain viable. In in vitro cell culture systems, CPE is evident when cells, as part of a confluent monolayer, show regions of non-confluence after contact with a specimen that contains a virus. The observed microscopic effect is generally focal in nature and the foci are initiated by a single virion. However, depending upon viral load in the sample, CPE may be observed throughout the monolayer after a sufficient period of incubation. Cells demonstrating viral induced CPE usually change morphology to a., rounded shape, and over a prolonged period of time can die and be released form their anchorage points in the monolayer. When many cells reach the point of focal destruction, the area is called a viral plaque, which appears as a hole in the monolayer. The terms "plaque" and "focus of viral infection" refer to a defined area of CPE which is usually the result of infection of the cell monolayer with a single infectious virus which then replicates and spreads to adjacent cells of the monolayer. Cytopathic effects are readily discernable and distinguishable by those skilled in the art.

Data provided herein also demonstrate that the exemplary transgenic BGMK-hDAF cells of the invention show increased sensitivity for infection by enteroviruses as compared to BGMK cells from which the invention's transgenic cells were derived. The term "sensitivity" and "sensitive" when made in reference to a cell is a relative term which refers to the degree of permissiveness of the cell to a virus as compared to the degree of permissiveness of another cell to the same virus.

For example, the term "increased sensitivity to enterovirus" when used in reference to the invention's transgenic BGMK cell lines refers to an increase, preferably at least a 5%, more preferably from 5% to 10,000%, more preferably from 5% to 1,000%, yet more preferably from 10% to 200%, and even more preferably from 10% to 100%, increase in the quantity of enterovirus protein, enterovirus nucleic acid, and/or of CPE by progeny virus which is produced following infection of the invention's transgenic BGMK cells with the enterovirus, as compared with the quantity of enterovirus protein, enterovirus nucleic acid, and/or of CPE by progeny virus (respectively) which is produced following infection of control BGMK cells. For example, if 34 samples containing one or more enteroviruses were tested for the presence of progeny virus, with 25 and 13 samples showing the presence of CPE using the invention's transgenic BGMK cells and control BGMK cells, respectively, then the sensitivity is 74% and 38% for the invention's transgenic BGMK cells and control BGMK cells, respectively. This reflects an increase of 90% in the sensitivity of the invention's transgenic BGMK cells as compared to the sensitivity of control BGMK cells (see, for example, Example 7, Table 9).

Also, the term "increased sensitivity to enterovirus" when used in reference to the invention's transgenic CV-1 cell lines refers to an increase, preferably at least a 5%, more preferably from 5% to 10,000%, more preferably from 5% to 1,000%, yet more preferably from 10% to 200%, and even more preferably from 10% to 100%, increase in the quantity of enterovirus protein, enterovirus nucleic acid, and/or of CPE by progeny virus which is produced following infection of the invention's transgenic CV-1 cells with the enterovirus, as compared with the quantity of enterovirus protein, enterovirus nucleic acid, and/or of CPE by progeny virus (respectively) which is produced following infection of control CV-1 cells.

B. Cultures Containing Transgenic Cells of the Invention

The invention provides single-cell type cultures of either transgenic BGMK cells or CV-1-hDAF cells for detecting the presence of enteroviruses. The term "single-cell type culture" refers to a composition, whether liquid, gel, or solid, which contains a single type of cell. Data presented herein demonstrates that the exemplary BGMK-hDAF cell line was more sensitive to enteroviruses in clinical samples than any other single-cell type culture tested.

The invention further provides mixed-cell type cultures which contain a cell type other than the transgenic BGMK cells of the invention in combination with the invention's transgenic BGMK cells. The invention also provides mixed-cell type cultures which contain a cell type other than the transgenic CV-1 cells of the invention in combination with the invention's transgenic CV-1 cells. These mixed-cell type cultures are useful for detecting the presence of enteroviruses and/or other organisms (including viruses, bacteria, protozoa).

As used herein, the term "mixed-cell type culture" refers to a composition, whether liquid, gel, or solid, which contains a mixture of two or more types of cells wherein the cell types are mingled together. For example, a mixed-cell type culture may contain cells from different tissues or organs from the same species and same genus. Alternatively, a mixed-cell type culture may contain cells from different species in the same genus. Yet another alternative is that a mixed-cell type culture contain cells from a different genus. The present invention encompasses any combination of cell types suitable for the detection, identification, and/or quantitation of viruses in samples, including mixed cell cultures in which all of the cell types used are not genetically engineered, mixtures in which one or more of the cell types are genetically engineered and the remaining cell types are not genetically engineered, and mixtures in which all of the cell types are genetically engineered.

The term "cell type other than the transgenic buffalo green monkey kidney cell line" as used herein includes, without limitation, the BGMK cell line from Diagnostic Hybrids, Inc., catalog # 53; any cell type which is established from a cell type other than the BGMK cell line from Diagnostic Hybrids, Inc., catalog # 53; and any cell type established from the BGMK-hDAF cell line deposited as ATCC # PTA-4594. In particular, the term "cell type other than the transgenic buffalo green monkey kidney cell line" expressly includes CV-1 cells which either have not been transfected with the hDAF gene, or which have been transfected with a transgene containing one or more nucleotide sequences of interest. Also, the term "cell type other than the transgenic buffalo green monkey kidney cell line" expressly includes BGMK cells (Diagnostic Hybrids, Inc., catalog # 53) which either have not been transfected with the hDAF gene, or which have been transfected with a transgene containing one or more nucleotide sequences of interest. Further, the term "cell type other than the transgenic buffalo green monkey kidney cell line" expressly includes BGMK-hDAF cells deposited as ATCC # PTA-4594 and which have additionally been transfected with a transgene containing one or more nucleotide sequences of interest.

The term "cell type other than the transgenic African green monkey kidney cell line" as used herein includes, without limitation, the CV-1 cell line (ATCC #CCL 70); any cell type which is established from a cell type other than the CV-1 cell line (ATCC #CCL 70); and any cell type established from the CV-1-hDAF cell line. In particular, the term "cell type other than the transgenic African green monkey kidney cell line" expressly includes CV-1 cells which either have not been transfected with the hDAF gene, or which have been transfected with a transgene containing one or more nucleotide sequences of interest. This term also expressly includes BGMK cells (Diagnostic Hybrids, Inc., catalog # 53) which either have not been transfected with the hDAF gene, or which have been transfected with a transgene containing one or more nucleotide sequences of interest. Further, the term "cell type other than the transgenic Green African green monkey kidney cell line" expressly includes CV-1-hDAF cells and which have additionally been transfected with a transgene containing one or more nucleotide sequences of interest.

An advantage of using the invention's transgenic BGMK cells and/or transgenic CV-1 cells in mixed-cell-type culture is that such cultures provide rapid and sensitive assay systems in a single mixed-cell type unit that is both suitable for diagnostic assays as well as eliminates the need for multiple cell lines cultured in individual containers.

While not limiting the invention to any particular cell type, exemplary cell lines which may be used in mixed-cell type cultures with the invention's transgenic CV-1 cells and/or transgenic BGMK cells and which can detect enteroviruses and/or other viruses are listed in Table 1.

TABLE 1

Exemplary Cell Lines For Mixed-Cell Type Cultures With The Invention's Cell Lines

| Cell Line | ATCC No. | Source | Virus[a] |
|---|---|---|---|
| CCD-13 Lu | CCL200 | Lung, human | Herpes, entero, adeno, paramy |
| CCD-8 Lu | CCL201 | Lung, human | Herpes, entero, adeno, paramy |
| CCD-14 Br | CCL203 | Bronchiole, human | Herpes, entero, adeno, myxo, paramy |
| CCD-16 Lu | CCL204 | Lung, human | Herpes, entero, adeno, paramy |
| CCD-18 Lu | CCL205 | Lung, human | Herpes, entero, adeno, paramy |
| CCD-19 Lu | CCL210 | Lung, human | Herpes, entero, adeno, paramy |
| Hs888 Lu | CCL211 | Lung, human | Herpes, entero, adeno, paramy |
| MRC-9 | CCL212 | Lung, human | Herpes, entero, adeno, paramy |
| CCD-25 Lu | CCL215 | Lung, human | Herpes, entero, adeno, paramy |
| WiDr | CCL218 | Colon, adenocarcinoma, human | Herpes, entero, adeno |
| DLD-1 | CCL221 | Colon, adenocarcinoma, human | Herpes, entero, adeno |
| COLO205 | CCL222 | Colon, adenocarcinoma, human | Herpes, entero, adeno |
| HCT-15 | CCL222 | Colon, adenocarcinoma, human | Herpes, entero, adeno |
| SW 480 | CCL228 | Colon, adenocarcinoma, human | Herpes, entero, adeno |
| LOVO | CCL229 | Colon, adenocarcinoma, human | Herpes, entero, adeno |
| SW403 | CCL230 | Colon, adenocarcinoma, human | Herpes, entero, adeno |
| SW48 | CCL231 | Colon, adenocarcinoma, human | Herpes, entero, adeno |
| SW116 | CCL233 | Colon, adenocarcinoma, human | Herpes, entero, adeno |
| SW1463 | CCL234 | Colon, adenocarcinoma, human | Herpes, entero, adeno |
| SW837 | CCL235 | Rectum, adenocarcinoma, human | Herpes, entero, adeno |
| SW948 | CCL237 | Colon, adenocarcinoma, human | Herpes, entero, adeno |
| SW1417 | CCL238 | Colon, adenocarcinoma, human | Herpes, entero, adeno |
| FHs74 Int | CCL241 | Small intestine, adenocarcinoma, human | Herpes, entero, adeno |
| HCT-8 | CCL244 | Adenocarcinoma, ileococal | Herpes, entero, adeno |
| HCT-116 | CCL247 | Colon carcinoma, human | Herpes, entero, adeno |
| T84 | CCL248 | Colon carcinoma, human | Herpes, entero, adeno |
| NCI-H747 | CCL252 | Cecum, adenocarcinoma, human | Herpes, entero, adeno |
| NCI-H508 | CCL253 | Cecum, adenocarcinoma, human | Herpes, entero, adeno |
| LS123 | CCL255 | Colon, human, adenocarcinoma | Herpes, entero, adeno |
| CaCo-2 | HTB37 | Colon, adenocarcinoma, human | Herpes, entero, adeno |
| HT-29 | HTB38 | Colon, adenocarcinoma, human | Herpes, entero, adeno |
| SK-CO-1 | HTB39 | Colon, adenocarcinoma, human | Herpes, entero, adeno |
| HuTu 80 | HTB40 | Duodenum, adenocarcinoma, human | Herpes, entero, adeno |
| A253 | HTB41 | Epidemoid carcinoma | Herpes, entero, adeno, paramyo |

TABLE 1-continued

Exemplary Cell Lines For Mixed-Cell Type Cultures With The Invention's Cell Lines

| Cell Line | ATCC No. | Source | Virus[a] |
|---|---|---|---|
| A704 | HTB45 | Kidney adenocarcinoma, human | Herpes, entero, adeno, paramyo |
| Hela | CCL2 | Epitheloid carcinoma, cervix, human | Herpes, entero, adeno, myxo, paramy |
| Hela | CCL2.1 | Epitheloid carcinoma, cervix, human | Herpes, entero, adeno, myxo, paramy |
| Hela53 | CCL2.2 | Epitheloid carcinoma, cervix, human | Herpes, entero, adeno, myxo, paramy |
| L-132 | CCL5 | Embryonic lung, human, Hela marker | Herpes, entero, adeno, myxo, paramy |
| Intestine | CCL6 | Embryonic intestine, human, Hela marker | Herpes, entero, adeno |
| BHK-21 | CCL10 | Kidney, synister or golden hamster | Herpes, entero, adeno, myxo, paramy |
| Hak | CCL15 | Kidney, syn hamster | Herpes, entero, adeno, myxo, paramy |
| KB | CCL17 | Epidermoid carcinoma oral, human | Herpes, entero, adeno, paramy |
| Hep-2 | CCL23 | Epidermoid carcinoma larynx, human | Herpes, entero, adeno, paramy |
| Wish | CCL25 | Ammion, human | Herpes, entero, adeno |
| Detroit 532 | CCL54 | Skin, human | Herpes, entero, adeno |
| FL | CCL62 | Ammion, human | Herpes, entero |
| Detroit 525 | CCL65 | Skin, human | Herpes, entero, adeno |
| Detroit 529 | CCL66 | Skin, human | Herpes, entero, adeno |
| Detroit 510 | CCL72 | Skin, human | Herpes, entero, adeno |
| WI-38 | CCL75 | Lung, diploid human | Herpes, entero, adeno, paramy |
| WI-38 VA13 | CCL75.1 | Lung, diploid human, SV-40 transformed | Herpes, entero, adeno, paramy |
| Citrullinemia | CCL76 | Skin, human | Herpes, entero, adeno, paramy |
| Spik (NBL-10) | CCL78 | Kidney, dolphin | Herpes, entero, adeno |
| Detroit 539 | CCL84 | Skin, human | Herpes, entero, adeno |
| Cridu Chat | CCL90 | Skin, human | Herpes, entero, adeno |
| W126 VA4 | CCL95.1 | Lung, human | Herpes, entero, adeno, paramy |
| BeWo | CCL98 | Choriocarcinoma, human | Herpes, entero, adeno |
| SW-13 | CCL105 | Adenocarcinoma, human, adrenal cortex | Herpes, entero, adeno |
| Detroit 548 | CCL116 | Skin | Herpes, entero, adeno |
| Detroit 573 | CCL117 | Skin | Herpes, entero, adeno |
| HT-1080 | CCL121 | Fibrocarcinoma, human | Herpes, entero, adeno |
| HG 261 | CCL122 | Skin, human | Herpes, entero, adeno |
| C211 | CCL123 | Skin, human | Herpes, entero, adeno |
| Amdur II | CCL124 | Skin, human | Herpes, entero, adeno |
| CHP 3 (M.W.) | CCL132 | Skin, human, fibroid like | Herpes, entero, adeno |
| CHP 4 (W.W.) | CCL133 | Skin, human, fibroid like | Herpes, entero, adeno |
| RD | CCL136 | Rhabdomyosarcoma | Herpes, entero, adeno |
| HEL 299 | CCL137 | Lung, diploid | Herpes, entero, adeno, paramy |
| Detroit 562 | CCL138 | Carcinoma, pharynx | Herpes, entero, adeno, myxo, paramy |
| MRC-5 | CCL171 | Lung, diploid, human | Herpes, entero, adeno, paramy |
| A-549 | CCL185 | Lung, carcinoma, human | Herpes, entero, adeno, myxo, paramy |
| IMR-90 | CCL186 | Lung, carcinoma, human | Herpes, entero, adeno, myxo, paramy |
| LS180 | CCL187 | Colon, adenocarcinoma, human | Herpes, entero, adeno |
| LS174T | CCL188 | Colon, adenocarcinoma, human | Herpes, entero, adeno |

[a]Herpes = Herpes viruses
Entero = Enteroviruses
Adeno = Adenoviruses
Myxo = Myxoviruses
Paramy = Paramyxoviruses In one preferred embodiment, the mixed-cell type culture used for detection of enteroviruses contains the invention's transgenic cell lines in combination with one or more of the following cell types: RD cells (ATCC #CCL-136), H292 cells (ATCC #CCL-1848), A549 cells (ATCC #CCL-185), MRC-5 cells (ATCC #CCL-171), CaCo-2 cells (ATCC #HTB-37). In a yet more preferred embodiment, the cell type is Caco-2 cells. As demonstrated herein, mixed-cell type cultures containing Caco-2 cells and the invention's exemplary BGMk-hDAF cells were more sensitive to enteroviruses in clinical samples than any other commercially available mixed-cell type culture tested. Methods for preparing mixed-cell type cultures are known in the art, such as those disclosed in U.S. Pat. No. 5,939,253 issued on Aug. 17, 1999 to Scholl et al., and U.S. Pat. No. 6,168,915 issued on Jan. 2, 2001 to Scholl et al., the entire contents of which are herein incorporated by reference. Briefly, cell line monolayers are cultured to confluence. The terms "confluence" and "confluent" as used herein in reference to an adherent cell line define a condition wherein cells throughout a culture are in contact with each other creating what appears to be a continuous sheet or "monolayer" of cells. The cell monolayers are rinsed with Hank's Balanced Salt Solution (HBSS) without magnesium or calcium. Depending upon the cell line, the cells may be dissociated by adding trypsin (0.125% in HBSS, without calcium or magnesium) or trypsin-EDTA (0.25% in 1 mM EDTA in HBSS, without calcium or magnesium) directly to the cell monolayer, and incubating for approximately 5 minutes at ambient temperature. Cell culture medium is added to each trypsinized cell suspension and the cells are repeatedly pipetted in order to produce near-single cell suspensions (i.e., without cell aggregates). Each trypsinized cell suspension is diluted in an adequate volume of culture medium to produce an optical density of cell suspension suitable to produce a confluent monolayer of cells within 2-3 days of incubation in a 96-well microtiter plate.

Mixed-cell type monolayers may be produced by co-plating two distinct cell types at an equal volume of each diluted cell suspension (e.g, 0.1 ml of each cell type is used to inoculate each well of a 96-well microtiter plate). The cells are allowed to attach to the well surface by gravity for 30-60 minutes, and the inoculated microtiter plates are incubated for up to three days at 36° C. in 5% $CO_2$ with 95% relative humidity.

Periodically during incubation, the mixed-cell type monolayers are checked for overall viability and for the ability of the cell lines to co-exist and develop as a single cell sheet (i.e., a single monolayer), with two distinct cell morphologies (i.e., dimorphic cell sheets), at an approximately equal density of each cell type. At confluence, the cells may be treated with a methylene blue staining solution to fix the cells and stain them a light blue in order to provide contrast for visualization using light microscopy.

Mixed-cell type cultures preferably contain a mixed cell monolayer adhered to the well surfaces. The adhered monolayer cultures may exhibit a smooth, evenly distributed monolayer, with each cell type being easily distinguished and surviving in a mixed-cell type monolayer, giving the appearance of a single cell distribution. Alternatively, the adhered monolayer cultures may exhibit two distinct morphologies at confluence, in which separate, distinct patches of each cell line co-exist within the monolayer, giving the appearance of oil mixing with water.

C. Infection of Cell Cultures and Detection of Enteroviruses in Cell Cultures

Following the incubation of the single-cell type or mixed-cell type monolayers, the monolayers are inoculated with specimens suspected of containing enterovirus or with a stock viral culture (i.e., a positive control). Negative or uninfected control cultures may also be employed; these cultures receive culture medium lacking any enterovirus. To inoculate a culture, an aliquot of the specimen to be tested is placed in a suitable standard culture medium in standard culture vessels.

Inoculation may be performed using any method suitable for the type of culture employed (i.e., plate, shell vial or tube culture). When plate cultures or shell vials are employed, solutions suspected of containing enterovirus (or known control solutions) are dispensed into the wells of the plates and the shell vials may be centrifuged for about 1 hour at 700 g at room temperature. When tube cultures are employed this centrifugation step is not required. Following "inoculation" (i.e., exposure of the monolayer to a specimen containing or suspected of containing infectious virus), the monolayers are incubated at 37° C. for a sufficient period of time (e.g., from about 3 hours to about 5 days) for the virus infectious cycle to proceed. The presence of enterovirus in the specimen may be detected by, for example, observing CPE.

EXPERIMENTAL

The following examples serve to illustrate certain preferred embodiments and aspects of the present invention and are not to be construed as limiting the scope thereof.

Example 1

Generation of Transgenic H292 and Buffalo Green Monkey Kidney (BGMK) Cells Which Express Human Decay Accelerating Factor (hDAF)

Monolayers of human mucoepidermoid cells (NCI-H292; also referred to as "H292" cells; ATCC # CCL-1848) and BGMK cells (Diagnostic Hybrids, Inc., catalog # 53) were individually subcultured with the help of trypsin, seeded into 12-well plates in the presence of E-MEM culture medium (Diagnostic Hybrids Inc.), and incubated at 36° C. incubator for 48 hr. The freshly formed cell monolayer was used for transfection.

The hDAF gene (GenBank Accession # M15799) was cloned in pcDNA3 (Invitrogen) using standard molecular biological techniques. The plasmid DNA of pcDNA3-DAF was used to transform *E. Coli*, and bacterial colonies which contained the plasmid DNA were selected and expanded by growing in broth culture for 18 hr. The plasmid DNA was purified from the bacteria using a commercial kit (Qiagen Inc.) and was used to transfect H292 and BGMK cells with SUPERFECT™ (Qiagen Inc.) as a carrier following the manufacturers instructions to generate H292-hDAF and BGMK-hDAF cells, respectively.

Transfected cells were incubated for another two days and Geneticin (G418) (Gibco-BRL Inc.) was added to select stable transfectants. After 10 days, most of the cells died and the surviving cells began to grow. Once the cells reformed a monolayer, they were subcultured. A portion of the cells was used to test for hDAF expression by staining with anti hDAF monoclonal antibody (PharMingen) as a primary antibody and fluorescein (FITC) conjugated goat anti-mouse IgG (Chemicon International Inc.) as a secondary antibody. In BGMK-hDAF cells, about 20% expressed hDAF, while H292-hDAF cells showed the same level of hDAF expression as in the untransfected parental H292 cells. Transfected cells expressed hDAF at different levels.

In order to enrich cells expressing human hDAF, H292-hDAF and BGMK-hDAF cells cultured in flasks were removed by trypsinization, labeled with anti-hDAF monoclonal antibody and FITC conjugated goat anti-mouse IgG (Chemicon), and then sorted by fluorescence activated cell sorting (FACS) to select for cells of relatively high hDAF expression. The small number of cells obtained by FACS was then cultured in a well of a 12-well culture plate. The cultures were expanded by serial subculture, and the expression of hDAF was monitored by immunofluorescence staining as described above and in FIG. 1.

In FIG. 1, apple-green fluorescence indicates expression of the hDAF protein by the positive cells. Most of the BGMK-hDAF cells expressed hDAF (FIG. 1A). In contrast, the untransfected BGMK cells only showed a dark green background (FIG. 1B), confirming that untransfected BGMK cells do not express hDAF. FIGS. 1C and D also shows that H292 and H292-hDAF cells showed almost identical staining intensity indicating that there were no significant difference in the level of hDAF expression between these cells.

To confirm the stability of expression in the transgenic cell lines, BGMK-hDAF and H292-hDAF cells were subcultured several times and monitored for hDAF expression. In BGMK-hDAF cells, the level of hDAF expression remained stable for at least 50 passages. These BGMK-hDAF cells were subsequently cloned by limiting dilution. Both H292 and H292-hDAF cells maintained the same level of hDAF expression after 50 passages.

Example 2

Detection of *Enterovirus* Isolates Using BGMK-hDAF Cells

Figure 2:
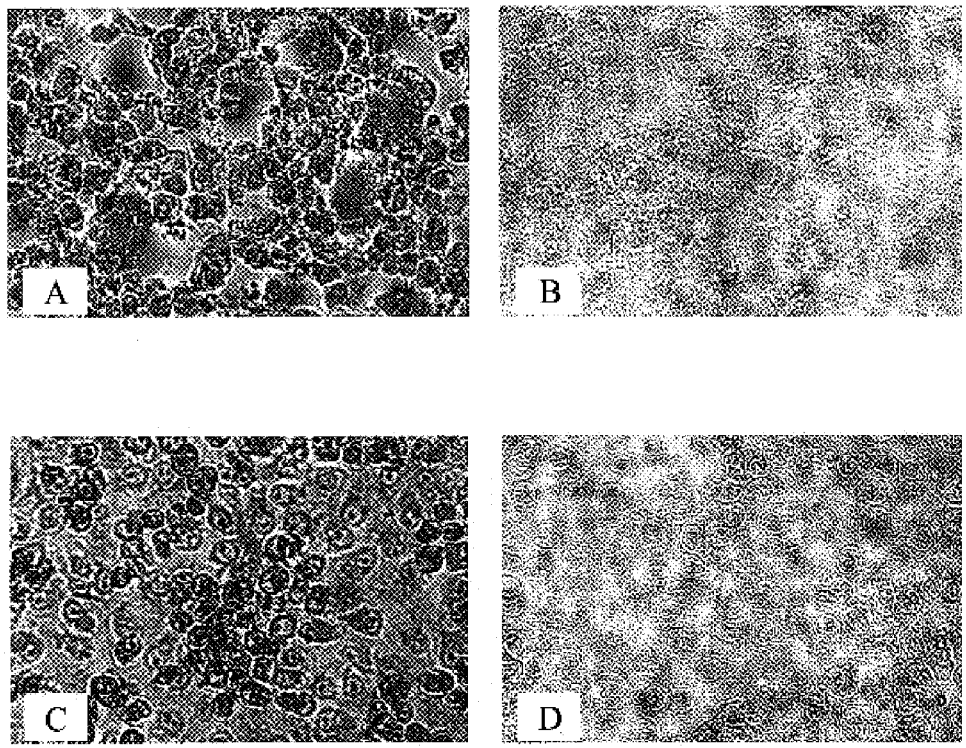
FIG. 2 is a photograph showing cytopathic effect (CPE) of (A) BGMK cells in the absence of echovirus, (B) BGMK in the presence of echovirus, (C) BGMK-hDAF cells in the absence of echovirus, and (D) BGMK-hDAF cells in the presence of echovirus.

To compare the sensitivity for the detection of enteroviruses by BGMK-hDAF cells with the parental BGMK cells, the cytopathic effect of isolates of echoviruses and of Coxsackie viruses on each cell type was determined as follows. Briefly, each cell type was seeded at a density of $2 \times 10^5$ cells/ml onto a 48-well plate using 0.2 ml per well. After the cells formed a monolayer (usually about 2-3 days), they were inoculated with serial dilutions of different isolates of enteroviruses. The inoculated cells were centrifuged at 700×g for 45 min at 22° C. then incubated at 36° C. in a 5% $CO_2$ incubator. The extent of cytopathic effect (CPE) induced by enterovirus infection was recorded daily. The typical CPE of enteroviruses was observed under the microscope as reflectile, small cells as shown in FIGS. 2B and D. Both the control BGMK and BGMK-hDAF cells showed a similar CPE, demonstrating that hDAF expression does not alter the character of the parent BGMK cells in that these cells continue to be infected by enteroviruses.

A. Echoviruses

The CPE results for echoviruses are shown in Table 2. The values in Table 2 (and Tables 3-8 infra) reflect the proportion of cells in the well which show a cytopathic effect (CPE) upon visual observation. In particular, – means 0%, 1+ means up to about 25%, 2+ means from about 25% to about 50%, 3+ means from about 50% to about 75%, and 4+ means from about 75% to 100% of the cells in the well show a cytopathic effect.

TABLE 2

Detection of Echoviruses Using BGMK (BG) Cells And BGMK-hDAF (BG-D) Cells

|  |  | DAY 1 | | DAY 2 | | DAY 3 | |
| --- | --- | --- | --- | --- | --- | --- | --- |
|  | * | BG | BG-D | BG | BG-D | BG | BG-D |
| Echo-4 | -1 | 1+ | 2+ | 2+ | 3+ | 3+ | 3+ |
|  |  | 1+ | 2+ | 2+ | 3+ | 3+ | 3+ |
|  | -2 | 1+ | 2+ | 1+ | 2+ | 2+ | 2+ |
|  |  | 1+ | 2+ | 1+ | 2+ | 2+ | 2+ |

TABLE 2-continued

Detection of Echoviruses Using BGMK (BG) Cells And BGMK-hDAF (BG-D) Cells

|  |  | BG | BG-D | BG | BG-D | BG | BG-D |
| --- | --- | --- | --- | --- | --- | --- | --- |
|  | -3 | — | 1+ | — | 1+ | 2+ | 2+ |
|  |  | — | 1+ | — | 1+ | 2+ | 2+ |
|  | -4 | — | — | — | — | 2+ | 1+ |
|  |  | — | — | — | — | 1+ | 1+ |
|  | -5 | — | — | — | — | 1+ | 1+ |
|  |  | — | — | — | — | 1+ | 1+ |
|  | -6 | — | — | — | — | — | — |
|  |  | — | — | — | — | — | — |
| Echo-6 | -1 | — | 4+ | — | 4+ | — | 4+ |
|  |  | — | 4+ | — | 4+ | — | 4+ |
|  | -2 | — | 4+ | — | 4+ | — | 4+ |
|  |  | — | 4+ | — | 4+ | — | 4+ |
|  | -3 | — | 4+ | — | 4+ | — | 4+ |
|  |  | — | 4+ | — | 4+ | — | 4+ |
|  | -4 | — | 4+ | — | 4+ | — | 4+ |
|  |  | — | 4+ | — | 4+ | — | 4+ |
|  | -5 | — | 1+ | — | 4+ | — | 4+ |
|  |  | — | 1+ | — | 4+ | — | 4+ |
|  | -6 | — | 1+ | — | 4+ | — | 4+ |
|  |  | — | 1+ | — | 4+ | — | 4+ |
|  | -7 | — | 1+ | — | 4+ | — | 4+ |
|  |  | — | — | — | 4+ | — | 4+ |
|  | -8 | — | — | — | 4+ | — | 4+ |
|  |  | — | — | — | — | — | — |
| Echo-7 | -1 | 1+ | 2+ | 4+ | 4+ | 4+ | 4+ |
|  |  | 1+ | 2+ | 4+ | 4+ | 4+ | 4+ |
|  | -2 | 1+ | 2+ | 2+ | 4+ | 4+ | 4+ |
|  |  | 1+ | 2+ | 2+ | 4+ | 4+ | 4+ |
|  | -3 | — | 1+ | 1+ | 2+ | 4+ | 4+ |
|  |  | — | 1+ | 1+ | 2+ | 2+ | 4+ |
|  | -4 | — | — | 1+ | 1+ | 2+ | 4+ |
|  |  | — | — | 1+ | 1+ | 1+ | 4+ |
|  | -5 | — | — | — | — | — | 3+ |
|  |  | — | — | — | — | — | 3+ |
|  | -6 | — | — | — | — | — | 2+ |
|  |  | — | — | — | — | — | — |
|  | -7 | — | — | — | — | — | — |
|  |  | — | — | — | — | — | — |

|  |  | DAY 1 | | DAY 2 | | DAY 3 | |
| --- | --- | --- | --- | --- | --- | --- | --- |
|  | * | BG | BG-D | BG | BG-D | BG | BG-D |
| Echo-9 | -1 | 2+ | 3+ | 4+ | 4+ | 4+ | 4+ |
|  |  | 2+ | 3+ | 4+ | 4+ | 4+ | 4+ |
|  | -2 | 1+ | 2+ | 4+ | 4+ | 4+ | 4+ |
|  |  | 1+ | 2+ | 4+ | 4+ | 4+ | 4+ |
|  | -3 | — | 1+ | 3+ | 3+ | 4+ | 4+ |
|  |  | — | 1+ | 3+ | 3+ | 4+ | 4+ |
|  | -4 | — | — | 2+ | 2+ | 3+ | 3+ |
|  |  | — | — | 2+ | 2+ | 3+ | 3+ |
|  | -5 | — | — | 1+ | 1+ | 2+ | 2+ |
|  |  | — | — | — | — | — | — |
|  | -6 | — | — | — | — | — | — |
|  |  | — | — | — | — | — | — |
|  | -7 | — | — | — | — | — | — |
|  |  | — | — | — | — | — | — |
|  | -8 | — | — | — | — | — | — |
|  |  | — | — | — | — | — | — |
| Echo-11 | -1 | — | 4+ | — | 4+ | — | 4+ |
|  |  | — | 4+ | — | 4+ | — | 4+ |
|  | -2 | — | 4+ | — | 4+ | — | 4+ |
|  |  | — | 4+ | — | 4+ | — | 4+ |
|  | -3 | — | 3+ | — | 4+ | — | 4+ |
|  |  | — | 3+ | — | 4+ | — | 4+ |
|  | -4 | — | 2+ | — | 4+ | — | 4+ |
|  |  | — | 2+ | — | 4+ | — | 4+ |
|  | -5 | — | 1+ | — | 4+ | — | 4+ |
|  |  | — | 1+ | — | 4+ | — | 4+ |
|  | -6 | — | 1+ | — | 3+ | — | 4+ |
|  |  | — | 1+ | — | 3+ | — | 4+ |
|  | -7 | — | — | — | 1+ | — | 2+ |
|  |  | — | — | — | 1+ | — | 3+ |
|  | -8 | — | — | — | — | — | — |
|  |  | — | — | — | — | — | — |

TABLE 2-continued

Detection of Echoviruses Using BGMK (BG) Cells And BGMK-hDAF (BG-D) Cells

| | | DAY 1 | | DAY 2 | | DAY 3 | |
|---|---|---|---|---|---|---|---|
| | * | BG | BG-D | BG | BG-D | BG | BG-D |
| Echo-30 | -1 | 2+ | 4+ | 4+ | 4+ | 4+ | 4+ |
| | | 2+ | 4+ | 4+ | 4+ | 4+ | 4+ |
| | -2 | 2+ | 4+ | 4+ | 4+ | 4+ | 4+ |
| | | 2+ | 4+ | 4+ | 4+ | 4+ | 4+ |
| | -3 | 1+ | 3+ | 4+ | 4+ | 4+ | 4+ |
| | | 1+ | 3+ | 4+ | 4+ | 4+ | 4+ |
| | -4 | 1+ | 3+ | 3+ | 4+ | 4+ | 4+ |
| | | 1+ | 3+ | 3+ | 4+ | 4+ | 4+ |
| | -5 | 1+ | 3+ | 2+ | 4+ | 3+ | 4+ |
| | | — | 3+ | — | 4+ | — | 4+ |
| | -6 | — | 1+ | — | 4+ | — | 4+ |
| | | — | 1+ | — | 4+ | — | 4+ |
| | -7 | — | 1+ | — | — | — | 3+ |
| | | — | — | — | 3+ | — | 3+ |
| | -8 | — | — | — | — | — | — |
| | | — | — | — | — | — | — |

* Fold dilution of sample; −1 means a $10^{-1}$ dilution, −2 means a $10^{-2}$ dilution, −3 means a $10^{-3}$ dilution, −4 means a $10^{-4}$ dilution, −5 means a $10^{-5}$ dilution, −6 means a $10^{-6}$ dilution, −7 means a $10^{-7}$ dilution, and −8 means a $10^{-8}$ dilution.

For echovirus-4 and echovirus-9, Table 2 shows that the final virus titers detected were approximately the same for BGMK and BGMK-hDAF. However, 10 fold higher dilution of virus was detected in BGMK-hDAF cells at day 1 compared to BGM cells.

For echovirus-7 and echovirus-30, the final virus titer detected by day 3 was from about 15 fold to about 20 fold higher for BGMK-hDAF cells than for BGMK cells. In addition to the detection of a higher dilution of these echoviruses, BGMK-DAF also showed earlier detection of higher dilutions of these echoviruses.

For echovirus-6 and echovirus-11, BGMK cells failed to detect these two viruses. Importantly, in contrast, BGMK-hDAF cells detected highly diluted virus by day 1. While not intending to limit the invention to any particular mechanism, these results indicate that hDAF is essential for entry of these two viruses into BGMK cells.

B. Coxsackie Viruses

BGMK cells are the most sensitive cell line for the detection of Coxsackie B 10 viruses and some Coxsackie A viruses. BGMK and BGMK-hDAF were compared for the detection of Coxsackie viruses A9, B1, B2, B4, and B5. The results are shown in Table 3.

TABLE 3

Detection of Coxsackie Viruses Using BGMK (BG) Cells And BGMK-hDAF (BG-D) Cells

| | | DAY 1 | | DAY 2 | | DAY 3 | |
|---|---|---|---|---|---|---|---|
| | * | BG | BG-D | BG | BG-D | BG | BG-D |
| Cox B1 | -1 | 2+ | 4+ | 4+ | 4+ | 4+ | 4+ |
| | | 2+ | 4+ | 4+ | 4+ | 4+ | 4+ |
| | -2 | 1+ | 4+ | 4+ | 4+ | 4+ | 4+ |
| | | 1+ | 4+ | 4+ | 4+ | 4+ | 4+ |
| | -3 | 1+ | 4+ | 4+ | 4+ | 4+ | 4+ |
| | | 1+ | 4+ | 4+ | 4+ | 4+ | 4+ |
| | -4 | 1+ | 3+ | 4+ | 4+ | 4+ | 4+ |
| | | 1+ | 3+ | 4+ | 4+ | 4+ | 4+ |
| | -5 | — | 2+ | 4+ | 4+ | 4+ | 4+ |
| | | — | 2+ | 4+ | 4+ | 4+ | 4+ |
| | -6 | — | 1+ | 2+ | 4+ | 4+ | 4+ |
| | | — | 1+ | 2+ | 4+ | 4+ | 4+ |
| | -7 | — | — | — | 2+ | — | 4+ |
| | | — | — | — | — | — | — |
| Cox B2 | -1 | 3+ | 4+ | 4+ | 4+ | 4+ | 4+ |
| | | 3+ | 4+ | 4+ | 4+ | 4+ | 4+ |
| | -2 | 3+ | 4+ | 4+ | 4+ | 4+ | 4+ |
| | | 3+ | 4+ | 4+ | 4+ | 4+ | 4+ |
| | -3 | 2+ | 3+ | 4+ | 4+ | 4+ | 4+ |
| | | 2+ | 3+ | 4+ | 4+ | 4+ | 4+ |
| | -4 | 2+ | 2+ | 4+ | 4+ | 4+ | 4+ |
| | | 2+ | 2+ | 4+ | 4+ | 4+ | 4+ |
| | -5 | 1+ | 1+ | 4+ | 4+ | 4+ | 4+ |
| | | 1+ | 1+ | 4+ | 4+ | 4+ | 4+ |
| | -6 | 1+ | 1+ | 3+ | 3+ | 4+ | 4+ |
| | | — | 1+ | 3+ | 3+ | 4+ | 4+ |
| | -7 | — | 1+ | — | 2+ | 3+ | 4+ |
| | | — | — | — | — | — | — |
| Cox B4 | -1 | 3+ | 3+ | 4+ | 4+ | 4+ | 4+ |
| | | 3+ | 3+ | 4+ | 4+ | 4+ | 4+ |
| | -2 | 3+ | 3+ | 4+ | 4+ | 4+ | 4+ |
| | | 3+ | 3+ | 4+ | 4+ | 4+ | 4+ |
| | -3 | 2+ | 2+ | 4+ | 4+ | 4+ | 4+ |
| | | 2+ | 2+ | 4+ | 4+ | 4+ | 4+ |
| | -4 | 1+ | 1+ | 4+ | 4+ | 4+ | 4+ |
| | | 1+ | 1+ | 4+ | 4+ | 4+ | 4+ |
| | -5 | 1+ | 1+ | 4+ | 4+ | 4+ | 4+ |
| | | — | — | 4+ | 4+ | 4+ | 4+ |
| | -6 | — | — | 2+ | 2+ | 4+ | 4+ |
| | | — | — | 2+ | 2+ | 4+ | 4+ |
| | -7 | — | — | — | — | 3+ | — |
| | | — | — | — | — | — | — |
| Cox B5 | -1 | 2+ | 4+ | 4+ | 4+ | 4+ | 4+ |
| | | 2+ | 4+ | 4+ | 4+ | 4+ | 4+ |
| | -2 | 2+ | 4+ | 4+ | 4+ | 4+ | 4+ |
| | | 2+ | 4+ | 4+ | 4+ | 4+ | 4+ |
| | -3 | 2+ | 4+ | 4+ | 4+ | 4+ | 4+ |
| | | 2+ | 4+ | 4+ | 4+ | 4+ | 4+ |
| | -4 | 1+ | 2+ | 4+ | 4+ | 4+ | 4+ |
| | | 1+ | 3+ | 4+ | 4+ | 4+ | 4+ |
| | -5 | — | 2+ | 4+ | 4+ | 4+ | 4+ |
| | | — | 2+ | 4+ | 4+ | 4+ | 4+ |
| | -6 | — | 1+ | 1+ | 4+ | 4+ | 4+ |
| | | — | — | 2+ | 4+ | 4+ | 4+ |
| | -7 | — | — | — | — | — | 4+ |
| | | — | — | — | — | — | — |
| Cox A9 | -1 | 2+ | 4+ | 4+ | 4+ | 4+ | 4+ |
| | | 2+ | 4+ | 4+ | 4+ | 4+ | 4+ |
| | -2 | 2+ | 4+ | 4+ | 4+ | 4+ | 4+ |
| | | 2+ | 4+ | 4+ | 4+ | 4+ | 4+ |
| | -3 | 2+ | 4+ | 4+ | 4+ | 4+ | 4+ |
| | | 2+ | 4+ | 4+ | 4+ | 4+ | 4+ |
| | -4 | 1+ | 4+ | 4+ | 4+ | 4+ | 4+ |
| | | 1+ | 4+ | 4+ | 4+ | 4+ | 4+ |
| | -5 | 1+ | 4+ | 4+ | 4+ | 4+ | 4+ |
| | | 1+ | 4+ | 4+ | 4+ | 4+ | 4+ |
| | -6 | — | 2+ | 4+ | 4+ | 4+ | 4+ |
| | | — | 2+ | 4+ | 4+ | 4+ | 4+ |
| | -7 | — | 1+ | 4+ | 4+ | 4+ | 4+ |
| | | — | 1+ | 4+ | 4+ | 4+ | 4+ |
| | -8 | — | 1+ | — | 4+ | — | 4+ |
| | | — | — | — | — | — | — |

For Coxsackie A9, B1 and B5, Table 3 shows that the BGMK-hDAF cells detected from about 15 fold to about 20 fold higher dilutions of virus at day one compared to BGMK cells. The final dilution of virus detected by day 3 was about the same for both cell types. For Coxsackie viruses B2 and B4, the BGMK-hDAF cells detected approximately the same dilution of virus as the BGMK cells. Without intending to limit the invention to any particular mechanism, these results indicate that hDAF probably does not enhance entry of these two viruses into BGM cells.

The above results demonstrate that BGMK-hDAF cells are capable of earlier detection of lower titers of enteroviruses than the control BGMK cells. These results also demonstrate that BGMK-hDAF cells are susceptible and permissive to some enteroviruses, such as echovirus-6 and echovirus-11, to which the parent BGMK cells were not permissive.

Example 3

Detection of Enteroviruses in Clinical Samples Using BGMK-hDAF Cells (Small Scale Investigation)

The above results using purified enterovirus isolates suggested to the inventors that BGMK-hDAF cells can enhance the early detection of low titer enteroviruses from the clinical specimen which is very important for patient management. To test whether this hypothesis may be applied to viruses present in clinical samples, the following experiment was carried out using clinical specimens.

BGMK and BGMK-hDAF cells were seeded onto a 48 well plate with $2 \times 10^5$ cells/ml using 0.2 ml per well and incubated in a 36° C., 5% $CO_2$ incubator for 3 days. Four previously tested enterovirus-positive original clinical samples were separately inoculated into the wells. The inoculated cells were centrifuged at 700×g for 45 min at 22° C. and incubated at 36° C. The cells were observed daily and CPE was recorded. The results are shown in Table 4.

TABLE 4

Detection of Enteroviruses From Clinical Specimens Using BGMK (BG) Cells and BGMK-hDAF (BG-D) Cells

| Virus Identified | Clinical Samples | DAY 1 | | DAY 2 | | DAY 3 | | DAY 4 | |
|---|---|---|---|---|---|---|---|---|---|
| | | BG | BG-D | BG | BG-D | BG | BG-D | BG | BG-D |
| Echo | 8326 | — | 1+ | — | 4+ | — | 4+ | — | 4+ |
| | | — | 1+ | — | 4+ | — | 4+ | — | 4+ |
| Echo | 4569 | — | 1+ | — | 4+ | — | 4+ | — | 4+ |
| | | — | 1+ | — | 4+ | — | 4+ | — | 4+ |
| Coxsackie | 3571 | — | — | — | 2+ | 2+ | 4+ | 4+ | 4+ |
| | | — | — | — | 2+ | — | 4+ | 4+ | 4+ |
| Coxsackie | 3348 | 1+ | 1+ | 2+ | 4+ | 4+ | 4+ | 4+ | 4+ |
| | | 1+ | 1+ | 3+ | 4+ | 4+ | 4+ | 4+ | 4+ |

Table 4 shows that BGM-hDAF cells detected three enterovirus-positive samples by day 1 whereas untransfected BGMK cells detected only one enterovirus-positive sample. By day 2, BGMK-DAF cells detected all four enterovirus-positive samples while BGMK cells only detected two enterovirus-positive samples by day 3. The specimens were typed using monoclonal antibody (Chemicon Inc.). Specimens 1 and 2 were typed to contain echoviruses and specimens 3 and 4 were typed to contain Coxsackie viruses.

These results clearly indicate that BGMK-hDAF cells not only detected enteroviruses earlier than BGMK cells, but also detected the presence of enteroviruses in a larger number of clinical specimens compared to BGMK cells as demonstrated by the earlier detection of enterovirus, and the higher number of enterovirus-positive samples which were detected.

Example 4

Detection of Enteroviruses in Clinical Samples Using BGMK-hDAF Cells (Large Scale Investigation)

The above encouraging results in Example 3 led the inventors to an evaluation of clinical specimens on a larger scale. BGMK and BGMK-hDAF cells were prepared as described in Example 3. The clinical specimens used in this example were from University Hospitals of Cleveland, Cleveland, Ohio, University of North Carolina, Chapel Hill, N.C. and Children's Hospital, Omaha, Nebr. A total of 17 specimens were inoculated. Due to the small volume of the original specimens, they were diluted 1 to 20 to generate enough volume for inoculation. After inoculation, the cells were treated as described in Example 3 and the cells were observed daily for CPE. The results are shown in Table 5.

TABLE 5

Detection Of Enteroviruses From Clinical Specimens Using BGMK (BG) Cells and BGMK-DAF (BG-D) Cells

| Virus Identified | Clinical Sample | BG | BG-D |
|---|---|---|---|
| Polio | 7142 | − | + |
| Coxsackie | 4856 | + | + |
| Echo | 7296 | − | + |
| Not typed | 4364 | + | − |
| Echo | 6707 | − | + |
| Echo | 8325 | − | + |
| Polio | 1234 | + | + |
| Echo | 9044 | + | + |
| Echo | 9039 | − | + |

TABLE 5-continued

Detection Of Enteroviruses From Clinical Specimens Using BGMK (BG) Cells and BGMK-DAF (BG-D) Cells

| Virus Identified | Clinical Sample | BG | BG-D |
|---|---|---|---|
| Echo | 8453 | + | + |
| Echo | 8642 | − | + |
| Echo | 9076 | − | + |
| Echo | 2707 | − | + |
| Echo/Coxs | 5514 | + | + |
| Echo | 8343 | − | + |
| Polio | 8335 | + | + |
| Not typed | 5669 | + | + |
| Total | | 8 | 16 |

Table 5 shows that BGMK cells detected 8 enterovirus-positive samples while BGMK-DAF detected 16 enterovirus-positive samples. One untyped enterovirus (specimen 4) detected by BGMK at day 5 was missed by BGMK-hDAF. The delay in, and lack of, detection by BGMK and BGMK-hDAF cells, respectively, indicated to the inventors that this was the result of very low titer specimens which may be related to the inoculum. Out of the 16 samples, 10 were typed to be echovirus, 3 were poliovirus, 1 was Coxsackie virus, 1 contained echovirus and Coxsackie virus, and 2 could not be typed.

These results, using larger clinical sample size, confirm the findings of Example 3 in that BGMK-hDAF cells are much more sensitive than BGMK cells for the detection of enteroviruses from clinical samples as demonstrated by the earlier detection of enterovirus, and the higher number of enterovirus-positive samples which were detected by BGMK-hDAF cells compared to BGMK cells.

Example 5

Detection of Isolates of Enteroviruses Using H292-hDAF Cells

The above results in Examples 2-4 indicated to the inventors that expression of hDAF on BGMK cells greatly enhanced the sensitivity of BGMK cells for the detection of enteroviruses. The experiments described in this Examples were carried out in order to determine whether the sensitivity of H292 cells to laboratory isolates of enteroviruses would also be enhanced by expression of additional copies of the hDAF gene.

The experiments described above in Example 2 were repeated using H292 and H292-hDAF cells instead of BGMK and BGMK-hDAF cells. Briefly, several echoviruses and Coxsackie viruses were serially diluted and inoculated into wells containing H292 and H292-hDAF cells and the CPE were observed daily. The results of these experiments are shown in Tables 6 and 7.

TABLE 6

Detection Of Echoviruses Using $H_{292}$ Cells and $H_{292}$-hDAF ($H_{292}$-D) Cells

| | | DAY 1 | | DAY 2 | | DAY 3 | |
|---|---|---|---|---|---|---|---|
| | * | $H_{292}$ | $H_{292}$-D | $H_{292}$ | $H_{292}$-D | $H_{292}$ | $H_{292}$-D |
| Echo-4 | −1 | 1+ | 1+ | 2+ | 2+ | 4+ | 4+ |
| | | 1+ | 1+ | 2+ | 2+ | 4+ | 4+ |
| | −2 | 1+ | 1+ | 2+ | 2+ | 3+ | 3+ |
| | | 1+ | 1+ | 2+ | 2+ | 3+ | 3+ |
| | −3 | — | — | 1+ | 1+ | 3+ | 3+ |
| | | — | — | 1+ | 1+ | 3+ | 3+ |
| | −4 | — | — | 1+ | 1+ | 3+ | 2+ |
| | | — | — | 1+ | 1+ | 3+ | 2+ |
| | −5 | — | — | — | — | 2+ | 2+ |
| | | — | — | — | — | 2+ | 1+ |
| | −6 | — | — | — | — | — | — |
| | | — | — | — | — | — | — |
| Echo-6 | −1 | 1+ | 1+ | 2+ | 2+ | 3+ | 3+ |
| | | 1+ | 1+ | 2+ | 2+ | 3+ | 3+ |
| | −2 | — | — | 1+ | 1+ | 2+ | 2+ |
| | | — | — | 1+ | 1+ | 2+ | 2+ |
| | −3 | — | — | 1+ | 1+ | 2+ | 2+ |
| | | — | — | 1+ | 1+ | 2+ | 2+ |
| | −4 | — | — | — | 1+ | 1+ | 1+ |
| | | — | — | — | — | 1+ | 1+ |
| | −5 | — | — | — | — | 1+ | 1+ |
| | | — | — | — | — | — | 1+ |

TABLE 6-continued

Detection Of Echoviruses Using $H_{292}$ Cells and $H_{292}$-hDAF ($H_{292}$-D) Cells

| | | | | | | |
|---|---|---|---|---|---|---|
| −6 | — | — | — | — | — | — |
| −7 | — | — | — | — | — | — |
| −8 | — | — | — | — | — | — |

| | | DAY 1 | | DAY 2 | | DAY 3 | |
|---|---|---|---|---|---|---|---|
| | * | $H_{292}$ | $H_{292}$-D | $H_{292}$ | $H_{292}$-D | $H_{292}$ | $H_{292}$-D |
| Echo-9 | −1 | 1+ | 1+ | 2+ | 2+ | 4+ | 4+ |
| | | 1+ | 1+ | 2+ | 2+ | 4+ | 4+ |
| | −2 | 1+ | 1+ | 2+ | 2+ | 4+ | 4+ |
| | | 1+ | 1+ | 2+ | 2+ | 4+ | 4+ |
| | −3 | — | — | 1+ | 1+ | 3+ | 3+ |
| | | — | — | — | 1+ | 3+ | 3+ |
| | −4 | — | — | — | — | 3+ | 3+ |
| | | — | — | — | — | — | 3+ |
| | −5 | — | — | — | — | — | — |
| | | — | — | — | — | — | — |
| | −6 | — | — | — | — | — | — |
| Echo-11 | −1 | 2+ | 2+ | 3+ | 3+ | 4+ | 4+ |
| | | 2+ | 2+ | 3+ | 3+ | 4+ | 4+ |
| | −2 | 1+ | 1+ | 2+ | 2+ | 4+ | 4+ |
| | | 1+ | 1+ | 2+− | 2+− | 4+− | 4+− |
| | −3 | — | — | 2+ | 2+ | 3+ | 3+ |
| | | — | — | 2+ | 2+ | 3+ | 3+ |
| | −4 | — | — | 2+ | 2+ | 3+ | 3+ |
| | | — | — | 2+ | 2+ | 3+ | 3+ |
| | −5 | — | — | 1+ | 1+ | 3+ | 3+ |
| | | — | — | — | — | 3+ | 3+ |
| | −6 | — | — | — | — | 2+ | 2+ |
| | | — | — | — | — | — | 2+ |
| | −7 | — | — | — | — | — | — |
| | | — | — | — | — | — | — |
| | −8 | | | | | | |

TABLE 7

Detection of Coxsackie Viruses Using $H_{292}$ Cells and $H_{292}$-hDAF ($H_{292}$-D) Cells

| | | DAY 1 | | DAY 2 | | DAY 3 | |
|---|---|---|---|---|---|---|---|
| | * | $H_{292}$ | $H_{292}$-D | $H_{292}$ | $H_{292}$-D | $H_{292}$ | $H_{292}$-D |
| Cox B1 | −1 | 2+ | 2+ | 2+ | 3+ | 4+ | 4+ |
| | | 2+ | 2+ | 3+ | 3+ | 4+ | 4+ |
| | −2 | 1+ | 2+ | 2+ | 3+ | 4+ | 4+ |
| | | 1+ | 1+ | 2+ | 3+ | 4+ | 4+ |
| | −3 | 1+ | 1+ | 2+ | 2+ | 4+ | 4+ |
| | | 1+ | 1+ | 2+ | 2+ | 4+ | 4+ |
| | −4 | — | — | 1+ | 1+ | 3+ | 3+ |
| | | — | — | 1+ | 1+ | 3+ | 3+ |
| | −5 | — | — | — | — | 2+ | 2+ |
| | | — | — | — | — | 2+ | 2+ |
| | −6 | — | — | — | — | 1+ | — |
| Cox B2 | −1 | — | — | 2+ | 2+ | 4+ | 4+ |
| | | — | — | 2+ | 2+ | 4+ | 4+ |
| | −2 | — | — | 1+ | 2+ | 2+ | 2+ |
| | | — | — | 1+ | 1+ | 2+ | 2+ |
| | −3 | — | — | 1+ | 1+ | 2+ | 2+ |
| | | — | — | 1+ | 1+ | 2+ | 2+ |
| | −4 | — | — | — | — | — | 1+ |
| | | — | — | — | — | — | — |
| | −5 | — | — | — | — | — | — |
| | | — | — | — | — | — | — |
| | −6 | — | — | — | — | — | — |

TABLE 7-continued

Detection of Coxsackie Viruses Using $H_{292}$ Cells and $H_{292}$-hDAF ($H_{292}$-D) Cells

| | | DAY 1 | | DAY 2 | | DAY 3 | |
|---|---|---|---|---|---|---|---|
| | * | $H_{292}$ | $H_{292\text{-}D}$ | $H_{292}$ | $H_{292}$-D | $H_{292}$ | $H_{292}$-D |
| | −7 | — | — | — | — | — | — |
| | | — | — | — | — | — | — |
| | −8 | — | — | — | — | — | — |
| | | — | — | — | — | — | — |
| Cox B4 | −1 | — | — | 1+ | 1+ | 2+ | 2+ |
| | | — | — | 1+ | 1+ | 2+ | 2+ |
| | −2 | — | — | 1+ | 1+ | 2+ | 2+ |
| | | — | — | 1+ | 1+ | 2+ | 2+ |
| | −3 | — | — | 1+ | 1+ | 1+ | 1+ |
| | | — | — | 1+ | 1+ | 1+ | 1+ |
| | −4 | — | — | — | — | 1+ | 1+ |
| | | — | — | — | — | 1+ | 1+ |
| | −5 | — | — | — | — | 1+ | 1+ |
| | | — | — | — | — | 1+ | 1+ |
| | −6 | — | — | — | — | — | — |
| | | — | — | — | — | — | — |
| | −7 | — | — | — | — | — | — |
| | | — | — | — | — | — | — |
| Cox B5 | −1 | 1+ | 1+ | 3+ | 3+ | 4+ | 4+ |
| | | 1+ | 1+ | 3+ | 3+ | 4+ | 4+ |
| | −2 | 1+ | 1+ | 3+ | 3+ | 4+ | 4+ |
| | | 1+ | 1+ | 3+ | 3+ | 4+ | 4+ |
| | −3 | — | — | 2+ | 2+ | 4+ | 4+ |
| | | — | — | 2+ | 2+ | 4+ | 4+ |
| | −4 | — | — | 2+ | 2+ | 4+ | 4+ |
| | | — | — | 2+ | 2+ | 4+ | 4+ |
| | −5 | — | — | 1+ | 1+ | 4+ | 4+ |
| | | — | — | 1+ | 1+ | 4+ | 2+ |
| | −6 | — | — | — | 1+ | 2+ | 2+ |
| | | — | — | — | — | 1+ | 2+ |

Tables 6 and 7 show that the sensitivity of detection of enteroviruses by H292 and H292-hDAF was unchanged with respect to the type of enterovirus isolate detected, the time of earliest enterovirus detection, and the number and identity of samples in which enteroviruses were detected.

These results demonstrate that transfection of additional copies of the hDAF gene into the H292 cells which express hDAF did not increase or decrease the cells' sensitivity for the detection of laboratory strains of enteroviruses. These results are in direct contrast to those obtained with BGMK-hDAF cells shown in Example 2 supra.

Example 6

Detection of Enteroviruses in Clinical Samples Using H292-hDAF Cells

In order to determine whether the sensitivity of H292-hDAF cells to enteroviruses in clinical samples was increased by expression of additional copies of the hDAF gene, four patient samples which had been tested to be positive for enteroviruses (the samples contained 2 echoviruses and 2 Coxsackie viruses) were incubated with H292 or H292-hDAF cells as described above, and the CPE were observed daily and recorded. The results are shown on Table 8.

TABLE 8

Detection of Enteroviruses Using $H_{292}$ Cells and $H_{292}$-hDAF ($H_{292}$-D) Cells

| Virus Identified | Clinical Samples | DAY 1 | | DAY 2 | | DAY 3 | |
|---|---|---|---|---|---|---|---|
| | | $H_{292}$ | $H_{292}$-D | $H_{292}$ | $H_{292}$-D | $H_{292}$ | $H_{292}$-D |
| Echo | 8326 | — | — | — | — | 1+ | 1+ |
| | | — | — | — | — | 1+ | 1+ |
| Echo | 4569 | — | — | — | — | 2+ | 1+ |
| | | — | — | — | — | — | 1+ |
| Coxsackie | 3571 | — | — | — | — | 1+ | 1+ |
| | | — | — | — | — | — | — |
| Coxsackie | 3348 | — | — | 1+ | 1+ | 2+ | 2+ |
| | | — | — | 1+ | — | 2+ | 2+ |

The profile of the results in Table 8 using clinical samples was similar to that with laboratory strains of enteroviruses. In other words, transfection of additional copies of the hDAF gene into H292 cells had no effect on the sensitivity of detection of enteroviruses from in clinical specimens by these cells.

Example 7

Detection of Enteroviruses in Mixed-Cell Type Cultures of BGMK-hDAF with Caco-2 Cells The sensitivity of BGMK-hDAF cells was compared to that of other single-cell type cultures and mixed-cell type cultures which are widely used for the detection of enteroviruses. E-Mix A contained RD cells (ATCC #CCL136) and H292 cells (ATCC #1848); E-Mix B contained BGMK cells (Diagnostic Hybrids, Inc.), and A549 cells (ATCC #CCL-185).

E-Mix A, E-Mix B, Caco$_2$/BGMK, and Caco-2/BGMK-hDAF cells were prepared in 48 well plates (Diagnostic Hybrids Inc.). MRC-5 and primary rhesus monkey kidney (pRhMK) cells were prepared in 48 well plates (ViroMed Inc.)

Thirty-four clinical samples which had previously tested positive for enteroviruses were used. The 34 enteroviruses were typed as 13 echoviruses, 14 Coxsackie viruses, 3 polioviruses, 1 enterovirus and 3 untyped enteroviruses by using echovirus blend, poliovirus blend, enterovirus blend and Coxsackie 13 blend from Chemicon International Inc. The 34 enteroviruses were also identified by PAN ENTERO blend (Chemicon) and enterovirus monoclonal antibody (Dako).

The clinical samples containing enteroviruses were diluted, and an inoculum of 0.2 ml was applied into wells containing the cells. The plates were centrifuged at 700×g for 45 min at 22° C. before incubation at 36° C. with 5% CO$_2$. The inoculated cells were visually observed daily and the cytopathic effect (CPE) was recorded from day 1 to 6. The results are shown in Table 9.

TABLE 9

Detection Of Enteroviruses From Clinical Samples[a] In Cell Culture[b]

| Day | E-Mix A | E-MixB | E-Mix A + B | CaCo2/ SBG | CaCo2/ BG | SBG | BG | MRC-5 | pRhMK | MRC-5 + pRhMK | CaCo2 |
|---|---|---|---|---|---|---|---|---|---|---|---|
| D1 | 9 (26%) | 13 (38%) | 14 (41%) | 24 (71%) | 14 (41%) | 25 (74%) | 13 (38%) | 5 (15%) | 4 (12%) | 6 (18%) | 4 (12%) |
| D2 | 12 (35%) | 19 (56%) | 22 (65%) | 30 (88%) | 22 (65%) | 30 (88%) | 17 (50%) | 9 (26%) | 9 (26%) | 13 (38%) | 10 (29%) |
| D3 | 16 (47%) | 27 (79%) | 29 (85%) | 33 (97%) | 29 (85%) | 33 (97%) | 20 (59%) | 16 (47%) | 17 (50%) | 24 (71%) | 21 (62%) |
| D4 | 16 (47%) | 27 (79%) | 29 (85%) | 33 (97%) | 29 (85%) | 33 (97%) | 21 (62%) | 16 (47%) | 18 (53%) | 24 (71%) | 22 (65%) |
| D5 | 16 (47%) | 27 (79%) | 29 (85%) | 33 (97%) | 29 (85%) | 33 (97%) | 21 (62%) | 16 (47%) | 19 (56%) | 26 (76%) | 23 (68%) |
| D6 | 16 (47%) | 27 (79%) | 29 (85%) | 33 (97%) | 29 (85%) | 33 (97%) | 21 (62%) | 16 (47%) | 20 (59%) | 26 (76%) | 23 (68%) |

[a]Values indicate the number of enterovirus-positive specimens as determined by detection of CPE on days 1 through 6 following incubation of the cells with the clinical specimen. Values in parentheses reflect the sensitivity of enterovirus detection as reflected by the number of enterovirus-positive specimens determined by detection of CPE divided by the total number (34) of specimens tested, expressed as a percentage.
[b]E-Mix A is RD cells and H292 cells; E-mixB is BGMK cells and A549 cells; SBG is BGMK-hDAF cells; BG is BGMK cells; and pRhMK is primary rhesus monkey kidney cells.

The results in Table 9 show that all 34 enteroviruses from the frozen specimens were isolated by one or more cells. A poliovirus specimen only appeared in pRhMK cells and not in other cells. The supernatant from the infected pRhMK cells was inoculated into all the other cells and they all propagated very well indicating low virus titer specimen rather than susceptibility problem of the other cells. In summary, Caco-2/BGMK-hDAF cells missed 1 poliovirus. E-Mix A plus E-Mix B missed 1 echovirus, 3 Coxsackie viruses and 1 poliovirus. MRC-5 plus pRhMK cells missed 3 echoviruses, 4 Coxsackie viruses and 1 poliovirus. Caco-2/BGMK cells missed 1 Coxsackie B virus, 3 echoviurses and 1 poliovirus.

Table 9 shows that BGMK-hDAF are more sensitive to enteroviruses in clinical samples than any of the other single-cell type cultures tested (i.e., BGMK cells, MRC-5 cells, primary rhesus monkey kidney cells, and Caco-2 cells). In particular, Table 9 confirms the above results in Examples 2 and 3 that BGMK-hDAF are more sensitive to enteroviruses in clinical samples than BGMK as shown by, for example, a sensitivity of 74% versus 38% on day 1, of 88% versus 50% on day 2, and of 97% versus 59% on day 3, respectively.

Table 9 also shows that BGMK-hDAF cells in single-cell type culture were more sensitive to enteroviruses in clinical samples than commercially available mixed-cell type cultures for enterovirus detection, including mixtures of RD and H292 cells (E-mix A), of BGMK and A549 cells (E-Mix B), of RD, H292, BGMK and A549 cells (E-mix A and B), and of MRC-5 and primary rhesus monkey kidney cells. Importantly, BGMK-hDAF cells not only detected more enterovirus-positive samples, but also detected enteroviruses earlier than with any other single-cell type culture or mixed-cell type culture tested. The data in Table 9 further shows that BGMK-hDAF cells retain their increased sensitivity to enteroviruses when combined in mixed-cell type culture with Caco-2 cells.

Example 8

Generation of Transgenic African Green Monkey Kidney (CV-1) Cells Which Express Human Decay Accelerating Factor (hDAF)

Monolayers of the African green monkey kidney (CV-1) cells (ATCC# CCL 70) were subcultured and seeded into 12-well plates in the presence of E-MEM culture medium (Diagnostic Hybrids Inc.) and incubated at 36° C. for 24 hrs. The freshly formed cell monolayer was used for transfection as described supra using the hDAF gene which was had been cloned in the pcDNA3 vector (Invitrogen) and using SUPERFECT™ as carrier of plasmid DNA (Quiagen Inc.) (Example 1). Transfected cells were incubated for 2 more days before the addition of Geneticin (G418) to select for stable transfectants. After 8 days, most of the cells died and surviving cells started to grow. In two more days the cells formed a monolayer. The expression of hDAF on the cell surface was assayed by immunofluorescent staining using anti-hDAF monoclonal antibody as primary antibody and fluorescein conjugated goat anti-mouse IgG (Chemicon International Inc.) as a secondary antibody. This revealed that about 5% of the transfected cells (which are referred to as CV-1-hDAF cells) expressed hDAF on the cell surface. The transfected cells were subsequently expanded and sorted by fluorescence activated cell sorting (FACS) to select cells with relatively high levels of hDAF expression. The small number of sorted cells were cultured and propagated. The cells were subcultured again and were diluted to seed one cell per well in 48 well plates. In about 2 weeks the cells formed a monolayer. These cell clones were subcultured and monitored for hDAF expression. The cloned cells with high hDAF expression were propagated and stored frozen at −80° C. These cloned cells are used for detection of enteroviruses.

From the above, it is clear that the invention provides cells which have enhanced sensitivity for enteroviruses and which are useful for rapid detection of enteroviruses. It is further clear that the invention also provides cells with a broad spectrum of permissiveness to enteroviruses, thus having the advantage of allowing simultaneous detection of several types of enteroviruses.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art and in fields related thereto are intended to be within the scope of the following claims.

The invention claimed is:

1. A method for detection of enterovirus in a sample, comprising:
   a) providing:
      i) a sample; and
      ii) a composition comprising a cell designated BGMK-hDAF and deposited as ATCC accession number PTA-4594;
   b) inoculating said cell with said sample to produce an inoculated cell; and
   c) observing said inoculated cell for the presence of said enterovirus.

2. The method of claim 1, wherein said composition further comprises a cell type other than said BGMK-hDAF cell (ATCC accession No. PTA-4594), and wherein said BGMK-hDAF cell (ATCC accession No. PTA-4594) and said cell type are in mixed-cell type culture.

3. The method of claim 2, wherein said cell type is chosen from one or more of RD cells, H292 cells, A549 cells, MRC-5 cells, KB cells, and CaCo-2 cells.

4. The method of claim 1, wherein said enterovirus is poliovirus.

5. The method of claim 1, wherein said enterovirus is Coxsackie A virus.

6. The method of claim 1, wherein said enterovirus is Coxsackie B virus.

7. The method of claim 1 5, wherein said enterovirus is echovirus.

8. The method of claim 1, wherein said enterovirus is chosen from one or more of enterovirus type 68, enterovirus type 69, enterovirus type 70, and enterovirus type 71.

9. A method for detection of one or more enterovirus in a sample, comprising:
   a) providing:
      i) a sample; and
      ii) a composition comprising a cell established from BGMK-hDAF cells (ATCC accession No. PTA-4594), wherein the established cell has a property chosen from one or more of (a) increased sensitivity to one or more enteroviruses compared to buffalo green monkey kidney cell line, and (b) permissiveness to echovirus chosen from one or more of echovirus-6 and echovirus-11;
   b) inoculating said established cell with said sample to produce an inoculated cell; and
   c) observing said inoculated cell for the presence of said one or more enterovirus.

10. The method of claim 9, wherein said composition further comprises a cell type other than said established cell, and wherein said established cell and said cell type are in mixed-cell type culture.

11. The method of claim 10, wherein said cell type is chosen from one or more of RD cells, H292 cells, A549 cells, MRC-5 cells, KB cells, and CaCo-2 cells.

12. The method of claim 10, wherein said cell type is CaCo-2 cells.

13. The method of claim 9, wherein said enterovirus is poliovirus.

14. The method of claim 9, wherein said enterovirus is Coxsackie A virus.

15. The method of claim 9, wherein said enterovirus is Coxsackie B virus.

16. The method of claim 9, wherein said enterovirus is echovirus.

17. The method of claim 9, wherein said enterovirus is chosen from one or more of enterovirus type 68, enterovirus type 69, enterovirus type 70, and enterovirus type 71.

18. The method of claim 9, wherein said established cell has the sensitivity to enterovirus as BGMK-hDAF cells (ATCC accession No. PTA-4594).

19. A method for detection of one or more enterovirus in a sample, comprising:

a) providing:

i) a sample; and ii) a composition comprising a transgenic buffalo green monkey kidney cell line expressing human decay accelerating factor, wherein said transgenic cell line has a property chosen from one or more of (a) increased sensitivity to one or more enteroviruses compared to buffalo green monkey kidney cell line, and (b) permissiveness to echovirus chosen from one or more of echovirus-6 and echovirus-11;

b) inoculating said transgenic cell line with said sample to produce an inoculated cell line; and c) observing said inoculated cell line for the presence of said one or more enterovirus.

20. The method of claim 19, wherein said composition further comprises a cell type other than said transgenic cell line, and wherein said transgenic cell line and said cell type are in mixed-cell type culture.

21. The method of claim 20, wherein said cell type is chosen from one or more of RD cells, H292 cells, A549 cells, MC-5 cells, KB cells, and CaCo-2 cells.

22. The method of claim 20, wherein said cell type is CaCo-2 cells.

23. The method of claim 19, wherein said enterovirus is poliovirus.

24. The method of claim 19, wherein said enterovirus is Coxsackie A virus.

25. The method of claim 19, wherein said enterovirus is Coxsackie B virus.

26. The method of claim 19, wherein said enterovirus is echovirus.

27. The method of claim 19, wherein said enterovirus is chosen from one or more of enterovirus type 68, enterovirus type 69, enterovirus type 70, and enterovirus type 71.

28. The method of claim 19, wherein said human decay accelerating factor is encoded by a sequence chosen from SEQ ID NO:1 and SEQ ID NO:3.

29. The method of claim 19, wherein said transgenic cell line has the sensitivity to enterovirus of the cell line designated as BGMK-hDAF (ATCC accession No. PTA-4594).

30. The method of claim 19, wherein said transgenic cell line is BGMK-hDAF (ATCC accession No. PTA-4594).

31. A method for producing one or more enterovirus, comprising:
   a) providing:
      i) a sample containing one or more enterovirus, and
      ii) a composition comprising a cell designated BGMK-hDAF and deposited as ATCC accession number PTA-4594; and
   b) inoculating said cell with said sample to produce an inoculated cell, wherein said inoculated cell produces one or more said enterovirus.

32. The method of claim 31, further comprising step c) isolating the produced one or more enterovirus.

33. The method of claim 31, wherein said enterovirus is poliovirus.

34. The method of claim 31, wherein said enterovirus is Coxsackie A virus.

35. The method of claim 31, wherein said enterovirus is Coxsackie B virus.

36. The method of claim 31, wherein said enterovirus is echovirus.

37. The method of claim 31, wherein said enterovirus is chosen from one or more of enterovirus type 68, enterovirus type 69, enterovirus type 70, and enterovirus type 71.

38. A method for producing one or more enterovirus, comprising:
   a) providing:
      i) a sample containing one or more enterovirus, and
      ii) a composition comprising a cell established from BGMK-hDAF (ATCC accession No. PTA-4594), wherein the established cell has a property chosen from one or more of (a) increased sensitivity to one or more enteroviruses compared to buffalo green monkey kidney cell line, and (b) permissiveness to echovirus chosen from one or more of echovirus-6 and echovirus-11; and
   b) inoculating said established cell with said sample to produce an inoculated cell, wherein said inoculated cell produces one or more said enterovirus.

39. The method of claim 38, further comprising step c) isolating the produced one or more enterovirus.

40. The method of claim 38, wherein said enterovirus is poliovirus.

41. The method of claim 38, wherein said enterovirus is Coxsackie A virus.

42. The method of claim 38, wherein said enterovirus is Coxsackie B virus.

43. The method of claim 38, wherein said enterovirus is echovirus.

44. The method of claim 38, wherein said enterovirus is chosen from one or more of enterovirus type 68, enterovirus type 69, enterovirus type 70, and enterovirus type 71.

45. The method of claim 38, wherein said established cell has the sensitivity to enterovirus as BGMK-hDAF cells (ATCC accession No. PTA-4594).

46. A method for producing one or more enterovirus, comprising:
   a) providing:
      i) a sample containing one or more enterovirus, and
      ii) a composition comprising a transgenic buffalo green monkey kidney cell line expressing human decay accelerating factor, wherein said transgenic cell line has a property chosen from one or more of (a) increased sensitivity to one or more enteroviruses compared to buffalo green monkey kidney cell line, and (b) permissiveness to echovirus chosen from one or more of echovirus-6 and echovirus-11; and
   b) inoculating said transgenic cell line with said sample to produce an inoculated cell, wherein said inoculated cell produces one or more said enterovirus.

47. The method of claim 46, further comprising step c) isolating the produced one or more enterovirus.

48. The method of claim 46, wherein said enterovirus is poliovirus.

49. The method of claim 46, wherein said enterovirus is Coxsackie A virus.

50. The method of claim 46, wherein said enterovirus is Coxsackie B virus.

51. The method of claim 46, wherein said enterovirus is echovirus.

52. The method of claim 46, wherein said enterovirus is chosen from one or more of enterovirus type 68, enterovirus type 69, enterovirus type 70, and enterovirus type 71.

53. The method of claim 46, wherein said human decay accelerating factor is encoded by a sequence chosen from SEQ ID NO:1 and SEQ ID NO:3.

54. The method of claim 46, wherein said transgenic cell line has the sensitivity to enterovirus of the cell line designated as BGMK-hDAF (ATCC accession No. PTA-4594).

55. The method of claim 46, wherein said transgenic cell line is BGMK-hDAF (ATCC accession No. PTA-4594).

* * * * *

SEQUENCE LISTING

<160> NUMBER OF SEQ ID NOS: 4

<210> SEQ ID NO 1
<211> LENGTH: 2017
<212> TYPE: DNA
<213> ORGANISM: Homo sapiens

<400> SEQUENCE: 1

| | | | | | |
|---|---|---|---|---|---|
| ccgagcgtgc | ccgcggcgct | gccctcctc | ggggagctgc | ccggctgct | gctgctggtg | 60 |
| ctgttgtgcc | tgccggccgt | gtggggtgac | tgtggcctcc | ccccagatgt | acctaatgcc | 120 |
| cagccagctt | tggaaggccg | tacaagtttt | cccgaggata | ctgtaataac | gtacaaatgt | 180 |
| gaagaaagct | ttgtgaaaat | tcctggcgag | aaggactcag | tgacctgcct | taagggcatg | 240 |
| caatggtcag | atattgaaga | gttctgcaat | cgtagctgcg | aggtgccaac | aaggctaaat | 300 |
| tctgcatccc | tcaaacagcc | ttatatcact | cagaattatt | ttccagtcgg | tactgttgtg | 360 |
| gaatatgagt | gccgtccagg | ttacagaaga | gaaccttctc | tatcaccaaa | actaacttgc | 420 |
| cttcagaatt | taaaatggtc | cacagcagtc | gaattttgta | aaaagaaatc | atgccctaat | 480 |
| ccgggagaaa | tacgaaatgg | tcagattgat | gtaccaggtg | gcatattatt | tggtgcaacc | 540 |
| atctccttct | catgtaacac | agggtacaaa | ttatttggct | cgacttctag | tttttgtctt | 600 |
| atttcaggca | gctctgtcca | gtggagtgac | ccgttgccag | agtgcagaga | aatttattgt | 660 |
| ccagcaccac | cacaaattga | caatggaata | attcaagggg | aacgtgacca | ttatggatat | 720 |
| agacagtctg | taacgtatgc | atgtaataaa | ggattcacca | tgattggaga | gcactctatt | 780 |
| tattgtactg | tgaataatga | tgaaggagag | tggagtggcc | caccacctga | atgcagagga | 840 |
| aaatctctaa | cttccaaggt | cccaccaaca | gttcagaaac | ctaccacagt | aaatgttcca | 900 |
| actacagaag | tctcaccaac | ttctcagaaa | accaccacaa | aaccaccac | accaaatgct | 960 |
| caagcaacac | ggagtacacc | tgtttccagg | acaaccaagc | attttcatga | acaaccccca | 1020 |
| aataaaggaa | gtggaaccac | ttcaggtact | acccgtcttc | tatctgggca | cacgtgtttc | 1080 |
| acgttgacag | gtttgcttgg | gacgctagta | accatgggct | tgctgacta | gccaaagaag | 1140 |
| agttaagaag | aaaatacaca | caagtataca | gactgttcct | agtttcttag | acttatctgc | 1200 |
| atattggata | aaataaatgc | aattgtgctc | ttcatttagg | atgctttcat | tgtctttaag | 1260 |
| atgtgttagg | aatgtcaaca | gagcaaggag | aaaaaaggca | gtcctggaat | cacattctta | 1320 |
| gcacacctgc | gcctcttgaa | aatagaacaa | cttgcagaat | tgagagtgat | tcctttccta | 1380 |
| aaagtgtaag | aaagcataga | gatttgttcg | tattaagaat | gggatcacga | ggaaaagaga | 1440 |
| aggaaagtga | tttttttcca | caagatctga | atgatatttt | ccactataaa | aggaaataaa | 1500 |
| aaatgaaaaa | cattatttgg | atatcaaaag | caaataaaaa | cccaattcag | tctcttctaa | 1560 |
| gcaaaattgc | taaagagaga | tgaccacatt | ataagtaat | ctttggctaa | ggcattttca | 1620 |
| tctttccttc | ggttggcaaa | atattttaaa | ggtaaaacat | gctggtgaac | cagggtgttg | 1680 |
| atggtgataa | gggaggaata | tagaatgaaa | gactgaatct | tcctttgttg | cacaaataga | 1740 |
| gtttggaaaa | agcctgtgaa | aggtgtcttc | tttgacttaa | tgtctttaaa | agtatccaga | 1800 |
| gatactacaa | tattaacata | agaaaagatt | atatattatt | tctgaatcga | gatgtccata | 1860 |
| gtcaaatttg | taaatcttat | tcttttgtaa | tatttattta | tatttattta | tgacagtgaa | 1920 |
| cattctgatt | ttcatgtaa | aacaagaaaa | gttgaagaag | atatgtgaag | aaaaatgtat | 1980 |
| ttttcctaaa | tagaaataaa | tgatcccatt | ttttggt | | | 2017 |

<210> SEQ ID NO 2
<211> LENGTH: 376
<212> TYPE: PRT
<213> ORGANISM: Homo sapiens

<400> SEQUENCE: 2

Pro Ser Val Pro Ala Leu Pro Leu Gly Glu Leu Pro Arg Leu
1               5                   10                  15

Leu Leu Leu Val Leu Leu Cys Leu Pro Ala Val Trp Gly Asp Cys Gly
            20                  25                  30

Leu Pro Pro Asp Val Pro Asn Ala Gln Pro Ala Leu Glu Gly Arg Thr
            35                  40                  45

Ser Phe Pro Glu Asp Thr Val Ile Thr Tyr Lys Cys Glu Glu Ser Phe
    50                  55                  60

Val Lys Ile Pro Gly Glu Lys Asp Ser Val Thr Cys Leu Lys Gly Met
65                  70                  75                  80

Gln Trp Ser Asp Ile Glu Glu Phe Cys Asn Arg Ser Cys Glu Val Pro
                85                  90                  95

Thr Arg Leu Asn Ser Ala Ser Leu Lys Gln Pro Tyr Ile Thr Gln Asn
            100                 105                 110

Tyr Phe Pro Val Gly Thr Val Val Glu Tyr Glu Cys Arg Pro Gly Tyr
            115                 120                 125

Arg Arg Glu Pro Ser Leu Ser Pro Lys Leu Thr Cys Leu Gln Asn Leu
    130                 135                 140

Lys Trp Ser Thr Ala Val Glu Phe Cys Lys Lys Ser Cys Pro Asn
145                 150                 155                 160

Pro Gly Glu Ile Arg Asn Gly Gln Ile Asp Val Pro Gly Gly Ile Leu
                165                 170                 175

Phe Gly Ala Thr Ile Ser Phe Ser Cys Asn Thr Gly Tyr Lys Leu Phe
            180                 185                 190

Gly Ser Thr Ser Ser Phe Cys Leu Ile Ser Gly Ser Ser Val Gln Trp
            195                 200                 205

Ser Asp Pro Leu Pro Glu Cys Arg Glu Ile Tyr Cys Pro Ala Pro Pro
210                 215                 220

Gln Ile Asp Asn Gly Ile Ile Gln Gly Glu Arg Asp His Tyr Gly Tyr
225                 230                 235                 240

Arg Gln Ser Val Thr Tyr Ala Cys Asn Lys Gly Phe Thr Met Ile Gly
                245                 250                 255

Glu His Ser Ile Tyr Cys Thr Val Asn Asn Asp Glu Gly Glu Trp Ser
            260                 265                 270

Gly Pro Pro Pro Glu Cys Arg Gly Lys Ser Leu Thr Ser Lys Val Pro
            275                 280                 285

Pro Thr Val Gln Lys Pro Thr Thr Val Asn Val Pro Thr Thr Glu Val
    290                 295                 300

Ser Pro Thr Ser Gln Lys Thr Thr Thr Lys Thr Thr Thr Pro Asn Ala
305                 310                 315                 320

Gln Ala Thr Arg Ser Thr Pro Val Ser Arg Thr Thr Lys His Phe His
                325                 330                 335

Glu Thr Thr Pro Asn Lys Gly Ser Gly Thr Thr Ser Gly Thr Thr Arg
            340                 345                 350

Leu Leu Ser Gly His Thr Cys Phe Thr Leu Thr Gly Leu Leu Gly Thr
            355                 360                 365

Leu Val Thr Met Gly Leu Leu Thr

```
                    370         375

<210> SEQ ID NO 3
<211> LENGTH: 2220
<212> TYPE: DNA
<213> ORGANISM: Homo sapiens

<400> SEQUENCE: 3
ccgctgggcg tagctgcgac tcggcggagt cccggcggcg cgtccttgtt ctaacccggc      60
gcgccatgac cgtcgcgcgg ccgagcgtgc ccgcggcgct gcccctcctc ggggagctgc     120
cccggctgct gctgctggtg ctgttgtgcc tgccggccgt gtggggtgac tgtggccttc     180
ccccagatgt acctaatgcc cagccagctt tggaaggccg tacaagtttt cccgaggata     240
ctgtaataac gtacaaatgt gaagaaagct ttgtgaaaat tcctggcgag aaggactcag     300
tgatctgcct taagggcagt caatggtcag atattgaaga gttctgcaat cgtagctgcg     360
aggtgccaac aaggctaaat tctgcatccc tcaaacagcc ttatatcact cagaattatt     420
ttccagtcgg tactgttgtg gaatatgagt gccgtccagg ttacagaaga gaaccttctc     480
tatcaccaaa actaacttgc cttcagaatt taaaatggtc cacagcagtc gaattttgta     540 aaagaaatc atgccctaat ccgggagaaa tacgaaatgg tcagattgat gtaccaggtg     600
gcatattatt tggtgcaacc atctccttct catgtaacac agggtacaaa ttatttggct     660
cgacttctag tttttgtctt atttcaggca gctctgtcca gtggagtgac ccgttgccag     720
agtgcagaga aatttattgt ccagcaccac cacaaattga caatggaata attcaagggg     780
aacgtgacca ttatggatat agacagtctg taacgtatgc atgtaataaa ggattcacca     840
tgattggaga gcactctatt tattgtactg tgaataatga tgaaggagag tggagtggcc     900
caccacctga atgcagagga aaatctctaa cttccaaggt cccaccaaca gttcagaaac     960
ctaccacagt aaatgttcca actacagaag tctcaccaac ttctcagaaa accaccacaa    1020
aaaccaccac accaaatgct caagcaacac ggagtacacc tgtttccagg acaaccaagc    1080
attttcatga acaaccccca aataaaggaa gtggaaccac ttcaggtact acccgtcttc    1140
tatctggttc tcgtcctgtc acccaggctg gtatgcggtg gtgtgatcgt agctcactgc    1200
agtctcgaac tcctgggttc aagcgatcct tccacttcag cctcccaagt agctggtact    1260
acagggcaca cgtgtttcac gttgacaggt ttgcttggga cgctagtaac catgggcttg    1320
ctgacttagc caaagaagag ttaagaagaa aatacacaca agtatacaga ctgttcctag    1380
tttcttagac ttatctgcat attggataaa ataaatgcaa ttgtgctctt catttaggat    1440
gctttcattg tctttaagat gtgttaggaa tgtcaacaga gcaaggagaa aaaaggcagt    1500
cctggaatca cattcttagc cacctacac ctcttgaaaa tagaacaact tgcagaattg    1560
agagtgattc ctttcctaaa agtgtaagaa agcatagaga tttgttcgta tttagaatgg    1620
gatcacgagg aaaagagaag gaaagtgatt ttttccaca agatctgtaa tgttatttcc     1680
acttataaag gaaataaaaa atgaaaaaca ttatttggat atcaaaagca ataaaaacc     1740 caattcagtc tcttctaagc aaaattgcta agagagatg aaccacatta taagtaatc     1800 tttggctgta aggcattttc atctttcctt cgggttggca aatattttta aggtaaaac     1860 atgctggtga accaggggtg ttgatggtga taagggagga atatagaatg aaagactgaa    1920
tcttcctttg ttgcacaaat agagtttgga aaaagcctgt gaaaggtgtc ttctttgact    1980
taatgtcttt aaaagtatcc agagatacta caatattaac ataagaaaag attatatatt    2040
atttctgaat cgagatgtcc atagtcaaat ttgtaaatct tattcttttg taatatttat    2100
```

```
ttatatttat ttatgacagt gaacattctg attttacatg taaaacaaga aaagttgaag    2160
aagatatgtg aagaaaaatg tattttcct aaatagaaat aaatgatccc atttttggt     2220
```

<210> SEQ ID NO 4
<211> LENGTH: 381
<212> TYPE: PRT
<213> ORGANISM: Homo sapiens

<400> SEQUENCE: 4

```
Met Thr Val Ala Arg Pro Ser Val Pro Ala Leu Pro Leu Leu Gly
 1               5                  10                  15

Glu Leu Pro Arg Leu Leu Leu Val Leu Leu Cys Leu Pro Ala Val
                20                  25                  30

Trp Gly Asp Cys Gly Leu Pro Pro Asp Val Pro Asn Ala Gln Pro Ala
                35                  40                  45

Leu Glu Gly Arg Thr Ser Phe Pro Glu Asp Thr Val Ile Thr Tyr Lys
     50                  55                  60

Cys Glu Glu Ser Phe Val Lys Ile Pro Gly Glu Lys Asp Ser Val Ile
 65                  70                  75                  80

Cys Leu Lys Gly Ser Gln Trp Ser Asp Ile Glu Glu Phe Cys Asn Arg
                 85                  90                  95

Ser Cys Glu Val Pro Thr Arg Leu Asn Ser Ala Ser Leu Lys Gln Pro
                100                 105                 110

Tyr Ile Thr Gln Asn Tyr Phe Pro Val Gly Thr Val Val Glu Tyr Glu
            115                 120                 125

Cys Arg Pro Gly Tyr Arg Arg Glu Pro Ser Leu Ser Pro Lys Leu Thr
    130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
                180                 185                 190

Gly Tyr Lys Leu Phe Gly Ser Thr Ser Ser Phe Cys Leu Ile Ser Gly
            195                 200                 205

Ser Ser Val Gln Trp Ser Asp Pro Leu Pro Glu Cys Arg Glu Ile Tyr
    210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
                260                 265                 270

Glu Gly Glu Trp Ser Gly Pro Pro Pro Glu Cys Arg Gly Lys Ser Leu
            275                 280                 285

Thr Ser Lys Val Pro Pro Thr Val Gln Lys Pro Thr Thr Val Asn Val
    290                 295                 300

Pro Thr Thr Glu Val Ser Pro Thr Ser Gln Lys Thr Thr Thr Lys Thr
305                 310                 315                 320

Thr Thr Pro Asn Ala Gln Ala Thr Arg Ser Thr Pro Val Ser Arg Thr
                325                 330                 335

Thr Lys His Phe His Glu Thr Thr Pro Asn Lys Gly Ser Gly Thr Thr
                340                 345                 350
```

```
Ser Gly Thr Thr Arg Leu Leu Ser Gly His Thr Cys Phe Thr Leu Thr
        355                 360                 365

Gly Leu Leu Gly Thr Leu Val Thr Met Gly Leu Leu Thr
        370             375             380
```